(12) United States Patent
Lillehaug et al.

(10) Patent No.: US 8,435,760 B2
(45) Date of Patent: May 7, 2013

(54) **SYSTEMS FOR EXPRESSION OF HETEROLOGOUS PROTEINS IN *M. CAPSULATUS***

(75) Inventors: Johan R. Lillehaug, Bergen (NO); Harald B. Jensen, Eidsvag (NO)

(73) Assignee: Stiftelsen Universitetsforskning, Bergen (NO)

( * ) Notice: Subject to any disclaimer, the term of this patent is extended or adjusted under 35 U.S.C. 154(b) by 26 days.

(21) Appl. No.: 12/677,888

(22) PCT Filed: Sep. 19, 2008

(86) PCT No.: PCT/NO2008/000337
§ 371 (c)(1), (2), (4) Date: Oct. 27, 2010

(87) PCT Pub. No.: WO2009/038475
PCT Pub. Date: Mar. 26, 2009

(65) Prior Publication Data
US 2011/0034671 A1 Feb. 10, 2011

(30) Foreign Application Priority Data
Sep. 18, 2007 (NO) .................................. 20074772

(51) Int. Cl.
*C12P 21/06* (2006.01)
*C07H 21/04* (2006.01)

(52) U.S. Cl.
USPC ....... 435/69.1; 435/69.3; 536/23.1; 536/23.4; 536/23.7

(58) Field of Classification Search .................. None
See application file for complete search history.

(56) References Cited

FOREIGN PATENT DOCUMENTS
WO  WO 02/055549 A2  7/2002

OTHER PUBLICATIONS

Whisstock et al., (Quarterly Reviews of Biophysics 2003, vol. 36 (3): 307-340 ).*
Devos et al., (Proteins: Structure, Function and Genetics, 2000, vol. 41: 98-107).*
Anne Fjellbirkeland et al. The C-terminal part of the surface-associated protein MopE of the methanotroph *Methylococcus capsulatus* (Bath) is secreted into the growth medium. *Arch Microbiol* (2001) 176:197-203.
Karlsen Odd A. The Surface-Associated and Secreted MopE Protein of *Methylococcus capsulatus* (Bath) Responds to Changes in the Concentration of Copper in the Growth Medium. Applied and Environmental Microbiology, Apr. 2003 vol. 69, No. 4. p. 2386-2388.

* cited by examiner

*Primary Examiner* — Padma V Baskar
(74) *Attorney, Agent, or Firm* — Dobe Law Group, LLC; Christopher Aniedobe

(57) ABSTRACT

The present invention relates to an expression system for the expression of proteins and peptides in a methanotrophic bacterium, preferably *M. capsulatus*. Further, the invention relates to the exportation and display of said peptides and proteins on the surface of said bacteria. The invention also describes a method for the production of a desired protein in *M. capsulatus*.

18 Claims, 12 Drawing Sheets

SEQUENCE LISTING

```
<160> NUMBER OF SEQ ID NOS: 33

<210> SEQ ID NO 1
<211> LENGTH: 540
<212> TYPE: PRT
<213> ORGANISM: Methylococcus capsulatus

<400> SEQUENCE: 1

Met Arg Asp Thr Met Asn Glu Lys His Cys Tyr Ser Leu Leu Ala Ala
1               5                   10                  15

Gly Leu Ile Ala Ala Val Pro Gln Leu Ala Ala Ala His Gly Gly Thr
            20                  25                  30

His Asp Val Thr Ala Val Ala His Leu Ser Tyr Ser Glu Ala Tyr Ser
        35                  40                  45

Glu Lys Leu Lys Lys Gly Gln Glu Val Gly Thr Glu Leu Leu Val Leu
    50                  55                  60

Asp Gly Arg Phe Glu Phe Asn Glu His Val Gly Met Gly Asp Ile Thr
65                  70                  75                  80

Pro Asp Thr Thr Trp Ser Ala Val Val Gln Gly Gln Thr Leu Ala Thr
                85                  90                  95

Gly Thr Leu Gly Asp Ala Thr Lys Lys Lys Phe Gly Ala Lys Gly Gly
            100                 105                 110

Met Ala Val Ile Asn Val Pro Gly Gly Thr Leu Lys Phe Thr Trp
            115                 120                 125

Asn Ala Lys Ala Ile Met Leu Lys Leu Lys Trp Thr Gly Glu Pro Ala
        130                 135                 140

Leu Ala Arg Leu Tyr Lys Asp Gln Asn Thr Ser Ile Asn Leu Pro Gln
145                 150                 155                 160

Phe Pro Val Asp Ile Ala Ile Gly Ser Leu His Gly Tyr Phe Asn Val
                165                 170                 175

Pro Val Thr Gly Gln Ala Lys Ala Thr Thr Lys Asn Gly Thr Met Leu
            180                 185                 190

Ser Lys Ile Ala Leu Lys Gly Thr Ala Asn Ser Ala Gly Leu Asp Thr
        195                 200                 205
```

Leu Asp Arg Asp Gly Asp Gly Ser Thr Ala Asp Ala Asp Cys Asn Asp
210                 215                 220

Phe Ala Pro Thr Ile His Pro Gly Ala Ala Glu Ala Thr Leu Asp Gly
225                 230                 235                 240

Val Asp Ser Asn Cys Asp Gly Arg Asp Ser Gly Val Ala Glu Val Val
                245                 250                 255

Glu Thr Phe Lys Asn Pro Gly Thr Tyr Ser Ser Pro Val Ile Asn Phe
            260                 265                 270

Lys Ile Ala Ser Pro Pro Gly Pro Gly Thr Pro Ile Tyr Gly Pro Pro
                275                 280                 285

Arg Asp Phe Ser Gly Tyr Asn Lys Ser Tyr Ser Leu Ala Ile Gly Lys
290                 295                 300

Thr Ser Tyr Tyr Asp Pro Thr Gly Thr Lys Trp Asn Asp Asp Thr
305                 310                 315                 320

Ile Thr Pro Val Ser Asp Gly Gln Asp Ile Trp Arg Gly Trp Thr His
                325                 330                 335

Thr Gly Lys Trp Ser Phe Phe Asn Gly Lys Ala Gly Asp Lys Ile Thr
                340                 345                 350

Leu Ser Val Gln Arg Asp Ala Gln Glu Ala Ser Leu Lys Gly Ala His
                355                 360                 365

Pro Gly Phe Ile Leu Phe Trp Arg Pro Glu Gly Pro Leu Phe Trp
370                 375                 380

Ala Gly Thr Gln Asp Leu Asp Glu Gly Gln Thr Ala Leu Pro Ala Asp
385                 390                 395                 400

Ser Asp Thr Val Ile Gly His Val Ile Val Gln His Ala Asp Trp Thr
                405                 410                 415

Leu Gln Gly Leu Pro Pro Lys Ala Asp His Thr Ala Pro Ala Gly Val
                420                 425                 430

Asp Thr Glu Leu Tyr Pro Met Lys Pro Asp Ser Tyr Thr Met Tyr Tyr
                435                 440                 445

Val Asp Ser Gly Tyr Asp Ala Asp Lys Tyr Val Ala Ser Lys Lys Leu
450                 455                 460

Ile Met His Pro Thr Ala Phe Lys Gly Leu Ala Leu Asn Asp Gly Thr
465                 470                 475                 480

Ala Gly Ala Phe Thr Lys Ser Ile Thr Leu Pro Lys Thr Gly Tyr Tyr
                485                 490                 495

Met Leu Tyr Val Ala Asn Val Leu Glu Val Asp Asp Trp Ser Val Asp
                500                 505                 510

Ala Asp Gly Lys Leu Thr Thr Thr Gly Glu Val Trp Glu Val Pro Ala
                515                 520                 525

Lys Gly Cys Trp Val Asn Ile Thr Ile Ser Lys Pro
530                 535                 540

<210> SEQ ID NO 2
<211> LENGTH: 337
<212> TYPE: PRT
<213> ORGANISM: Methylococcus capsulatus

<400> SEQUENCE: 2

His Gly Leu Asp Thr Leu Asp Arg Asp Gly Asp Gly Ser Thr Ala Asp
1               5                   10                  15

Ala Asp Cys Asn Asp Phe Ala Pro Thr Ile His Pro Gly Ala Ala Glu
                20                  25                  30

Ala Thr Leu Asp Gly Val Asp Ser Asn Cys Asp Gly Arg Asp Ser Gly
                35                  40                  45

```
Val Ala Glu Val Val Glu Thr Phe Lys Asn Pro Gly Thr Tyr Ser Ser
    50                  55                  60

Pro Val Ile Asn Phe Lys Ile Ala Ser Pro Pro Gly Pro Gly Thr Pro
 65                  70                  75                  80

Ile Tyr Gly Pro Pro Arg Asp Phe Ser Gly Tyr Asn Lys Ser Tyr Ser
                 85                  90                  95

Leu Ala Ile Gly Lys Thr Ser Tyr Tyr Asp Pro Thr Thr Gly Thr Lys
                100                 105                 110

Trp Asn Asp Asp Thr Ile Thr Pro Val Ser Asp Gly Gln Asp Ile Trp
            115                 120                 125

Arg Gly Trp Thr His Thr Gly Lys Trp Ser Phe Phe Asn Gly Lys Ala
        130                 135                 140

Gly Asp Lys Ile Thr Leu Ser Val Gln Arg Asp Ala Gln Glu Ala Ser
145                 150                 155                 160

Leu Lys Gly Ala His Pro Gly Phe Ile Leu Phe Trp Arg Pro Glu Gly
                165                 170                 175

Gly Pro Leu Phe Trp Ala Gly Thr Gln Asp Leu Asp Glu Gly Gln Thr
                180                 185                 190

Ala Leu Pro Ala Asp Ser Asp Thr Val Ile Gly His Val Ile Val Gln
            195                 200                 205

His Ala Asp Trp Thr Leu Gln Gly Leu Pro Pro Lys Ala Asp His Thr
        210                 215                 220

Ala Pro Ala Gly Val Asp Thr Glu Leu Tyr Pro Met Lys Pro Asp Ser
225                 230                 235                 240

Tyr Thr Met Tyr Tyr Val Asp Ser Gly Tyr Asp Ala Asp Lys Tyr Val
                245                 250                 255

Ala Ser Lys Lys Leu Ile Met His Pro Thr Ala Phe Lys Gly Leu Ala
                260                 265                 270

Leu Asn Asp Gly Thr Ala Gly Ala Phe Thr Lys Ser Ile Thr Leu Pro
            275                 280                 285

Lys Thr Gly Tyr Tyr Met Leu Tyr Val Ala Asn Val Leu Glu Val Asp
        290                 295                 300

Asp Trp Ser Val Asp Ala Asp Gly Lys Leu Thr Thr Thr Gly Glu Val
305                 310                 315                 320

Trp Glu Val Pro Ala Lys Gly Cys Trp Val Asn Ile Thr Ile Ser Lys
                325                 330                 335

Pro

<210> SEQ ID NO 3
<211> LENGTH: 1620
<212> TYPE: DNA
<213> ORGANISM: Methylococcus capsulatus

<400> SEQUENCE: 3
atgagagaca ccatgaacga aaagcattgc tactccttac tggccgccgg cctcatcgcc      60
gccgtgccgc aactcgcagc cgcccacgga ggcactcacg acgtcaccgc ggtcgcccac     120
ctgagctatt cggaagccta ttcggaaaag ctcaagaagg gtcaggaagt gggcaccgag     180
ctgctggtgc tggacggacg cttcgaattc aacgaacacg tcggcatggg tgacatcacc     240
ccggacacga cctggtcggc cgtcgtgcag ggccagaccc tggcaacggg taccctgggc     300
gacgccacca agaagaagtt cggcgccaag gcgggcatgg cggtgatcaa cgtgcccggc     360
ggcggtacgc tcaaattcac ctggaacgcc aaggccatca tgctcaagct gaaatggacc     420
ggcgagccgg ccttggcccg gctgtacaag gaccagaaca ccagcatcaa tctgccgcaa     480
```

```
ttcccggtcg acatcgcgat cggcagtctg cacggctact tcaacgttcc ggtcaccggc        540
caggcgaagg ccacgaccaa gaacggcacc atgctgtcca agatcgcctt gaaaggcaca        600
gcgaactccg cgggcctgga cacgctggac cgggacggcg acggctccac ggccgacgcc        660
gattgcaacg acttcgcgcc caccatccat ccggcgccg ccgaagcgac gctggacggc         720
gtggattcca actgcgacgg gcgcgactcc ggcgtggcgg aagtcgtcga gaccttcaag        780
aatccgggca cctactccag cccggtcatc aacttcaaga tcgcttcgcc gccggggccg        840
ggaacgccca tctacgggcc gccgcgtgat ttctccggtt acaacaagag ctactcgctg        900
gcgatcggca agacctcgta ctacgatccg accaccggca ccaagtggaa cgacgacacc        960
atcacgccgg tcagtgatgg tcaggacatc tggcgcggct ggacccatac cggcaagtgg       1020
tcgttcttca acggcaaggc cggcgacaag atcaccctca gcgtacagcg tgatgcgcag       1080
gaagccagcc tgaaaggcgc ccatccgggc ttcatcctgt tctggcggcc cgagggcggt       1140
ccgctgttct gggccggcac ccaggatctc gacgagggcc agaccgcgct gcccgccgac       1200
tccgacaccg ttatcggcca cgtgatcgtt cagcacgccg actggaccct gcagggcttg       1260
ccgcccaagg ccgaccatac cgcacccgcg ggcgtggata ccgagctcta tcccatgaag       1320
ccggacagct acaccatgta ctacgtcgac tccggctacg atgccgacaa gtacgtggca       1380
tcgaagaagc tcatcatgca ccccacggcg ttcaaagggc tggccctgaa cgacggcacc       1440
gccggggcgt tcaccaagtc catcacccctg ccgaagacgg gctattacat gctgtacgtc      1500
gccaacgtcc tggaagtgga cgactggagc gtcgacgcgg acggcaagct caccaccacc       1560
ggcgaagtct gggaagtgcc ggccaagggc tgctgggtca acatcacgat ctccaagccg       1620

<210> SEQ ID NO 4
<211> LENGTH: 1011
<212> TYPE: DNA
<213> ORGANISM: Methylococcus capsulatus

<400> SEQUENCE: 4
catggcctgg acacgctgga ccgggacggc gacggctcca cggccgacgc cgattgcaac          60
gacttcgcgc ccaccatcca tccgggcgcc gccgaagcga cgctggacgg cgtggattcc        120
aactgcgacg ggcgcgactc cggcgtggcg gaagtcgtcg agaccttcaa gaatccgggc        180
acctactcca gcccggtcat caacttcaag atcgcttcgc cgccggggcc gggaacgccc        240
atctacgggc cgccgcgtga tttctccggt tacaacaaga gctactcgct ggcgatcggc        300
aagacctcgt actacgatcc gaccaccggc accaagtgga cgacgacac catcacgccg         360 gtcagtgatg gtcaggacat ctggcgcggc tggacccata ccggcaagtg gtcgttcttc        420
aacggcaagg ccggcgacaa gatcaccctc agcgtacagc gtgatgcgca ggaagccagc        480
ctgaaaggcg cccatccggg cttcatcctg ttctggcggc ccgagggcgg tccgctgttc        540
tgggccggca cccaggatct cgacgagggc cagaccgcgc tgcccgccga ctccgacacc        600
gttatcggcc acgtgatcgt tcagcacgcc gactggaccc tgcagggctt gccgcccaag        660
gccgaccata ccgcacccgc gggcgtggat accgagctct atcccatgaa gccggacagc        720
tacaccatgt actacgtcga ctccggctac gatgccgaca agtacgtggc atcgaagaag        780
ctcatcatgc accccacggc gttcaaaggg ctggccctga cgacggcac cgccggggcg         840 ttcaccaagt ccatcacccct gccgaagacg gctattaca tgctgtacgt cgccaacgtc        900
ctggaagtgg acgactggag cgtcgacgcg gacggcaagc tcaccaccac cggcgaagtc       960
tgggaagtgc cggccaaggg ctgctgggtc aacatcacga tctccaagcc g                1011
```

<210> SEQ ID NO 5
<211> LENGTH: 6165
<212> TYPE: DNA
<213> ORGANISM: Methylococcus capsulatus

<400> SEQUENCE: 5

| | | | | | | |
|---|---|---|---|---|---|---|
| taatacgact | cactataggg | gaattgtgag | cggataacaa | ttcccctcta | gatgcatgct | 60 |
| cgagcggccg | ccagtgtgat | ggatatctgc | agaattcgcc | cttggcttgt | attgagctca | 120 |
| tccgaagata | agcgctttcc | gcgcagcccg | attctttcat | ggatcacgat | tccattgaat | 180 |
| gcggcgaaag | tctcagggtc | cggtcatgaa | tgaagagtta | tggcggccca | gtacgtcacc | 240 |
| gttatgtccg | atggctgtat | caaacaaaga | cacgtgtagt | gatatcggac | aactcgtcca | 300 |
| tccccgtcgg | agcattcgga | taacgtgctc | atcgttccaa | aatattgata | tacggtatac | 360 |
| gtatccgaag | aataaagttg | gcacgatccc | tgtaactagg | ttgtcacgac | ctcgtcggag | 420 |
| gttgtatgtc | cggtgttccg | tgacgtcatc | gggcattcat | cattcataga | atgtgttacg | 480 |
| gaggaaacaa | catatgagag | acaccatgaa | cgaaaagcat | tgctactcct | tactggccgc | 540 |
| cggcctcatc | gccgccgtgc | cgcaactcgc | agccgcccat | ggctagcatg | actggtggac | 600 |
| agcaaatggg | tcggatccgg | ctgctaacaa | agcccgaaag | gaagctgagt | tggctgctgc | 660 |
| caccgctgag | caataactag | cataaccccct | tggggcctct | aaacgggtct | tgaggggttt | 720 |
| tttgctgaaa | ggaggaacta | tatccggata | tcccgcaaga | ggcccggcag | taccggcata | 780 |
| accaagccta | tgcctacagc | atccagggtg | acggtgccga | ggatgacgat | gagcgcattg | 840 |
| ttagatttca | tacacggtgc | ctgactgcgt | tagcaattta | actgtgataa | actaccgcat | 900 |
| taaagcttat | cgatgataag | ctgtcaaaca | tgagaattct | tgaagacgaa | agggcctcgt | 960 |
| gatacgccta | tttttatagg | ttaatgtcat | gataataatg | gtttcttaga | cgtcaggtgg | 1020 |
| cacttttcgg | ggaaatgtgc | gcggaacccc | tatttgttta | tttttctaaa | tacattcaaa | 1080 |
| tatgtatccg | ctcatgagac | aataaccctg | ataaatgctt | caataatatt | gaaaaaggaa | 1140 |
| gagtatgagt | attcaacatt | tccgtgtcgc | ccttattccc | ttttttgcgg | cattttgcct | 1200 |
| tcctgttttt | gctcacccag | aaacgctggt | gaaagtaaaa | gatgctgaag | atcagttggg | 1260 |
| tgcacgagtg | ggttacatcg | aactggatct | caacagcggt | aagatccttg | agagttttcg | 1320 |
| ccccgaagaa | cgttttccaa | tgatgagcac | ttttaaagtt | ctgctatgtg | gcgcggtatt | 1380 |
| atcccgtgtt | gacgccgggc | aagagcaact | cggtcgccgc | atacactatt | ctcagaatga | 1440 |
| cttggttgag | tactcaccag | tcacagaaaa | gcatcttacg | gatggcatga | cagtaagaga | 1500 |
| attatgcagt | gctgccataa | ccatgagtga | taacactgcg | gccaacttac | ttctgacaac | 1560 |
| gatcggagga | ccgaaggagc | taaccgcttt | tttgcacaac | atgggggatc | atgtaactcg | 1620 |
| ccttgatcgt | tgggaaccgg | agctgaatga | agccatacca | aacgacgagc | gtgacaccac | 1680 |
| gatgcctgca | gcaatggcaa | caacgttgcg | caaactatta | actggcgaac | tacttactct | 1740 |
| agcttcccgg | caacaattaa | tagactggat | ggaggcggat | aaagttgcag | gaccacttct | 1800 |
| gcgctcggcc | cttccggctg | gctggtttat | tgctgataaa | tctggagccg | gtgagcgtgg | 1860 |
| gtctcgcggt | atcattgcag | cactggggcc | agatggtaag | ccctcccgta | tcgtagttat | 1920 |
| ctacacgacg | gggagtcagg | caactatgga | tgaacgaaat | agacagatcg | ctgagatagg | 1980 |
| tgcctcactg | attaagcatt | ggtaactgtc | agaccaagtt | tactcatata | tactttagat | 2040 |
| tgatttaaaa | cttcattttt | aatttaaaag | gatctaggtg | aagatccttt | ttgataatct | 2100 |
| catgaccaaa | atcccttaac | gtgagttttc | gttccactga | gcgtcagacc | ccgtagaaaa | 2160 |

```
gatcaaagga tcttcttgag atccttttttt tctgcgcgta atctgctgct tgcaaacaaa    2220
aaaaccaccg ctaccagcgg tggtttgttt gccggatcaa gagctaccaa ctcttttttcc   2280
gaaggtaact ggcttcagca gagcgcagat accaaatact gtccttctag tgtagccgta    2340
gttaggccac cacttcaaga actctgtagc accgcctaca tacctcgctc tgctaatcct    2400
gttaccagtg gctgctgcca gtggcgataa gtcgtgtctt accgggttgg actcaagacg    2460
atagttaccg gataaggcgc agcggtcggg ctgaacgggg ggttcgtgca cacagcccag    2520
cttggagcga acgacctaca ccgaactgag atacctacag cgtgagctat gagaaagcgc    2580
cacgcttccc gaagggagaa aggcggacag gtatccggta agcggcaggg tcggaacagg    2640
agagcgcacg agggagcttc caggggggaaa cgcctggtat ctttatagtc ctgtcgggtt    2700
tcgccacctc tgacttgagc gtcgattttt gtgatgctcg tcaggggggc ggagcctatg    2760
gaaaaacgcc agcaacgcgg cctttttacg gttcctggcc ttttgctggc cttttgctca    2820
catgttcttt cctgcgttat cccctgattc tgtggataac cgtattaccg cctttgagtg    2880
agctgatacc gctcgccgca gccgaacgac cgagcgcagc gagtcagtga gcgaggaagc    2940
ggaagagcgc ctgatgcggt attttctcct tacgcatctg tgcggtattt cacaccgcat    3000
atatggtgca ctctcagtac aatctgctct gatgccgcat agttaagcca gtatacactc    3060
cgctatcgct acgtgactgg gtcatggctg cgccccgaca cccgccaaca cccgctgacg    3120
cgccctgacg ggcttgtctg ctcccggcat ccgcttacag acaagctgtg accgtctccg    3180
ggagctgcat gtgtcagagg ttttcaccgt catcaccgaa acgcgcgagg cagctgcggt    3240
aaagctcatc agcgtggtcg tgaagcgatt cacagatgtc tgcctgttca tccgcgtcca    3300
gctcgttgag tttctccaga agcgttaatg tctggcttct gataaagcgg ccatgttaa     3360
gggcggtttt ttcctgtttg gtcactgatg cctccgtgta aggggggattt ctgttcatgg    3420
gggtaatgat accgatgaaa cgagagagga tgctcacgat acgggttact gatgatgaac    3480
atgcccggtt actggaacgt tgtgagggta acaactggc ggtatggatg cggcgggacc     3540
agagaaaaat cactcagggt caatgccagc gcttcgttaa tacagatgta ggtgttccac    3600
agggtagcca gcagcatcct gcgatgcaga tccggaacat aatggtgcag ggcgctgact    3660
tccgcgtttc cagactttac gaaacacgga aaccgaagac cattcatgtt gttgctcagg    3720
tcgcagacgt tttgcagcag cagtcgcttc acgttcgctc gcgtatcggt gattcattct    3780
gctaaccagt aaggcaaccc cgccagccta gccgggtcct caacgacagg agcacgatca    3840
tgcgcacccg tggccaggac ccaacgctgc ccgagatgcg ccgcgtgcgg ctgctggaga    3900
tggcggacgc gatggatatg ttctgccaag ggttggtttg cgcattcaca gttctccgca    3960
agaattgatt ggctccaatt cttggagtgg tgaatccgtt agcgaggtgc cgccggcttc    4020
cattcaggtc gaggtggccc ggctccatgc accgcgacgc aacgcgggga ggcagacaag    4080
gtataggcg gcgcctacaa tccatgccaa cccgttccat gtgctcgccg aggcggcata     4140
aatcgccgtg acgatcagcg gtccagtgat cgaagttagg ctggtaagag ccgcgagcga    4200
tccttgaagc tgtccctgat ggtcgtcatc tacctgcctg acagcatgg cctgcaacgc      4260
gggcatcccg atgccgccgg aagcgagaag aatcataatg gggaaggcca tccagcctcg    4320
cgtcgcgaac gccagcaaga cgtagcccag cgcgtcggcc gccatgccgg cgataatggc    4380
ctgcttctcg ccgaaacgtt tggtggcggg accagtgacg aaggcttgag cgagggcgtg    4440
caagattccg aataccgcaa gcgacaggcc gatcatcgtc gcgctccagc gaaagcggtc    4500
ctcgccgaaa atgacccaga gcgctgccgg cacctgtcct acgagttgca tgataaagaa    4560
```

```
gacagtcata agtgcggcga cgatagtcat gccccgcgcc caccggaagg agctgactgg    4620
gttgaaggct ctcaagggca tcggtcgaga tcccggtgcc taatgagtga gctaacttac    4680
attaattgcg ttgcgctcac tgcccgcttt ccagtcggga aacctgtcgt gccagctgca    4740
ttaatgaatc ggccaacgcg cggggagagg cggtttgcgt atttgggcgcc agggtggttt    4800 ttcttttcac cagtgagacg ggcaacagct gattgccctt caccgcctgg ccctgagaga    4860
gttgcagcaa gcggtccacg ctggtttgcc ccagcaggcg aaaatcctgt ttgatggtgg    4920
ttaacggcgg gatataacat gagctgtctt cggtatcgtc gtatcccact accgagatat    4980
ccgcaccaac gcgcagcccg gactcggtaa tggcgcgcat tgcgcccagc gccatctgat    5040
cgttggcaac cagcatcgca gtgggaacga tgccctcatt cagcatttgc atggtttgtt    5100
gaaaaccgga catggcactc cagtcgcctt cccgttccgc tatcggctga atttgattgc    5160
gagtgagata tttatgccag ccagccagac gcagacgcgc cgagacagaa cttaatgggc    5220
ccgctaacag cgcgatttgc tggtgaccca atgcgaccag atgctccacg cccagtcgcg    5280
taccgtcttc atgggagaaa ataatactgt tgatgggtgt ctggtcagag acatcaagaa    5340
ataacgccgg aacattagtg caggcagctt ccacagcaat ggcatcctgg tcatccagcg    5400
gatagttaat gatcagccca ctgacgcgtt gcgcgagaag attgtgcacc gccgctttac    5460
aggcttcgac gccgcttcgt tctaccatcg acaccaccac gctggcaccc agttgatcgg    5520
cgcgagattt aatcgccgcg acaatttgcg acggcgcgtg cagggccaga ctggaggtgg    5580
caacgccaat cagcaacgac tgtttgcccg ccagttgttg tgccacgcgg ttgggaatgt    5640
aattcagctc cgccatcgcc gcttccactt tttcccgcgt tttcgcagaa cgtggctgg    5700 cctggttcac cacgcgggaa acggtctgat aagagacacc ggcatactct gcgacatcgt    5760
ataacgttac tggtttcaca ttcaccaccc tgaattgact ctcttccggg cgctatcatg    5820
ccataccgcg aaaggttttg cgccattcga tggtgtccgg gatctcgacg ctctccctta    5880
tgcgactcct gcattaggaa gcagcccagt agtaggttga ggccgttgag caccgccgcc    5940
gcaaggaatg tgtcatgcaa ggagatggcg cccaacagtc ccccggccac ggggcctgcc    6000 accatacccca cgccgaaaca agcgctcatg agcccgaagt ggcgagcccg atcttcccca    6060
tcggtgatgt cggcgatata ggcgccagca accgcacctg tggcgccggt gatgccggcc    6120
acgatgcgtc cggcgtagag gatcgagatc tcgatcccgc gaaat    6165

<210> SEQ ID NO 6
<211> LENGTH: 7358
<212> TYPE: DNA
<213> ORGANISM: Methylococcus capsulatus

<400> SEQUENCE: 6
taatacgact cactatagggg gaattgtgag cggataacaa ttcccctcta gatgcatgct      60
cgagcggccg ccagtgtgat ggatatctgc agaattcgcc ctttaagagc tcatccgaag     120
ataagcgctt tccgcgcagc ccgattcttt catggatcac gattccattg aatgcggcga     180
aagtctcagg gtccggtcat gaatgaagag ttatggcggc ccagtacgtc accgttatgt     240
ccgatggctg tatcaaacaa agacacgtgt agtgatatcg gacaactcgt ccatccccgt     300
cggagcattc ggataacgtg ctcatcgttc caaaatattg atatacgtga tacgtatccg     360
aagaataaag ttggcacgat ccctgtaact aggttgtcac gacctcgtcg gaggttgtat     420
gtccggtgtt ccgtgacgtc atcgggcatt catcattcat agaatgtgtt acggaggaaa     480
caacatatga gagacaccat gaacgaaaag cattgctact ccttactggc cgccggcctc     540
```

```
atcgccgccg tgccgcaact cgcagccgcc catggcctgg acacgctgga ccggacggc      600
gacggctcca cggccgacgc cgattgcaac gacttcgcgc ccaccatcca tccgggcgcc     660
gccgaagcga cgctggacgg cgtggattcc aactgcgacg ggcgcgactc cggcgtggcg     720
gaagtcgtcg agaccttcaa gaatccgggc acctactcca gcccggtcat caacttcaag     780
atcgcttcgc cgccggggcc gggaacgccc atctacgggc cgccgcgtga tttctccggt     840
tacaacaaga gctactcgct ggcgatcggc aagacctcgt actacgatcc gaccaccggc     900
accaagtgga cgacgacac catcacgccg gtcagtgatg gtcaggacat ctggcgcggc      960
tggacccata ccggcaagtg gtcgttcttc aacggcaagg ccggcgacaa gatcaccctc    1020
agcgtacagc gtgatgcgca ggaagccagc ctgaaaggcg cccatccggg cttcatcctg    1080
ttctggcggc ccgagggcgg tccgctgttc tgggccggca cccaggatct cgacgagggc    1140
cagaccgcgc tgcccgccga ctccgacacc gttatcggcc acgtgatcgt tcagcacgcc    1200
gactggaccc tgcagggctt gccgcccaag gccgaccata ccgcacccgc gggcgtggat    1260
accgagctct atcccatgaa gccggacagc tacaccatgt actacgtcga ctccggctac    1320
gatgccgaca agtacgtggc atcgaagaag ctcatcatgc accccacggc gttcaaaggg    1380
ctggccctga cgacggcac cgccggggcg ttcaccaagt ccatcaccct gccgaagacg     1440
ggctattaca tgctgtacgt cgccaacgtc ctggaagtgg acgactggag cgtcgacgcg    1500
gacggcaagc tcaccaccac cggcgaagtc tgggaagtgc cggccaaggg ctgctgggtc    1560
aacatcacga tctccaagcc gtaaatccgg cttgatgtgc gtgatccttc ggagcggcca    1620
gtcgaccgtt ccgcggggaa acttccgga gccaatcccc gtcctctgcg gcggggattt     1680
ttttattcgg cggaaccgag ttgggcgacg gcttttttcca gcttcttcaa ccggctccag   1740
atttcgtgca ggctcgagat caccgccaaa gggcgaattc cagcacactg gcggccgtta    1800
ctagtggatc cggctgctaa caaagcccga aaggaagctg agttggctgc tgccaccgct    1860
gagcaataac tagcataacc ccttggggcc tctaaacggg tcttgagggg ttttttgctg    1920
aaaggaggaa ctatatccgg atatcccgca agaggcccgg cagtaccggc ataaccaagc    1980
ctatgcctac agcatccagg gtgacggtgc cgaggatgac gatgagcgca ttgttagatt    2040
tcatacacgg tgcctgactg cgttagcaat ttaactgtga taaactaccg cattaaagct    2100
tatcgatgat aagctgtcaa acatgagaat tcttgaagac gaaagggcct cgtgatacgc    2160
ctatttttat aggttaatgt catgataata atggtttctt agacgtcagg tggcacttttt   2220
cggggaaatg tgcgcggaac ccctatttgt ttatttttct aaatacattc aaatatgtat    2280
ccgctcatga caataaaccc ctgataaatg cttcaataat attgaaaaag gaagagtatg    2340
agtattcaac atttccgtgt cgcccttatt ccctttttttg cggcattttg ccttcctgtt   2400
tttgctcacc cagaaacgct ggtgaaagta aaagatgctg aagatcagtt gggtgcacga    2460
gtgggttaca tcgaactgga tctcaacagc ggtaagatcc ttgagagttt tcgccccgaa    2520
gaacgttttc caatgatgag cacttttaaa gttctgctat gtggcgcggt attatcccgt    2580
gttgacgccg ggcaagagca actcggtcgc cgcatacact attctcagaa tgacttggtt    2640
gagtactcac cagtcacaga aaagcatctt acggatggca tgacagtaag agaattatgc    2700
agtgctgcca taaccatgag tgataacact gcggccaact tacttctgac aacgatcgga    2760
ggaccgaagg agctaaccgc ttttttgcac aacatggggg atcatgtaac tcgccttgat    2820
cgttgggaac cggagctgaa tgaagccata ccaaacgacg agcgtgacac cacgatgcct    2880
gcagcaatgg caacaacgtt gcgcaaacta ttaactggcg aactacttac tctagcttcc    2940
```

```
cggcaacaat taatagactg gatggaggcg gataaagttg caggaccact tctgcgctcg   3000
gcccttccgg ctggctggtt tattgctgat aaatctggag ccggtgagcg tgggtctcgc   3060
ggtatcattg cagcactggg gccagatggt aagccctccc gtatcgtagt tatctacacg   3120
acggggagtc aggcaactat ggatgaacga aatagacaga tcgctgagat aggtgcctca   3180
ctgattaagc attggtaact gtcagaccaa gtttactcat atatacttta gattgattta   3240
aaacttcatt tttaatttaa aaggatctag gtgaagatcc ttttttgataa tctcatgacc   3300
aaaatccctt aacgtgagtt ttcgttccac tgagcgtcag accccgtaga aaagatcaaa   3360
ggatcttctt gagatccttt ttttctgcgc gtaatctgct gcttgcaaac aaaaaaacca   3420
ccgctaccag cggtggtttg tttgccggat caagagctac caactctttt tccgaaggta   3480
actggcttca gcagagcgca gataccaaat actgtccttc tagtgtagcc gtagttaggc   3540
caccacttca agaactctgt agcaccgcct acatacctcg ctctgctaat cctgttacca   3600
gtggctgctg ccagtggcga taagtcgtgt cttaccgggt tggactcaag acgatagtta   3660
ccggataagg cgcagcggtc gggctgaacg ggggggttcgt gcacacagcc cagcttggag   3720
cgaacgacct acaccgaact gagatacccta cagcgtgagc tatgagaaag cgccacgctt   3780
cccgaaggga gaaaggcgga caggtatccg gtaagcggca gggtcggaac aggagagcgc   3840
acgagggagc ttccagggggg aaacgcctgg tatctttata gtcctgtcgg gtttcgccac   3900
ctctgacttg agcgtcgatt tttgtgatgc tcgtcagggg ggcggagcct atggaaaaac   3960
gccagcaacg cggccttttt acggttcctg gccttttgct ggccttttgc tcacatgttc   4020
tttcctgcgt tatcccctga ttctgtggat aaccgtatta ccgcctttga gtgagctgat   4080
accgctcgcc gcagccgaac gaccgagcgc agcgagtcag tgagcgagga agcggaagag   4140
cgcctgatgc ggtattttct ccttacgcat ctgtgcggta tttcacaccg catatatggt   4200
gcactctcag tacaatctgc tctgatgccg catagttaag ccagtataca ctccgctatc   4260
gctacgtgac tgggtcatgg ctgcgccccg acacccgcca cacccgctg acgcgccctg   4320
acgggcttgt ctgctcccgg catccgctta cagacaagct gtgaccgtct ccgggagctg   4380
catgtgtcag aggttttcac cgtcatcacc gaaacgcgcg aggcagctgc ggtaaagctc   4440
atcagcgtgg tcgtgaagcg attcacagat gtctgcctgt tcatccgcgt ccagctcgtt   4500
gagtttctcc agaagcgtta atgtctggct tctgataaag cgggccatgt taagggcggt   4560
tttttcctgt ttggtcactg atgcctccgt gtaaggggga tttctgttca tgggggtaat   4620
gataccgatg aaacgagaga ggatgctcac gatacgggtt actgatgatg aacatgcccg   4680
gttactggaa cgttgtgagg gtaaacaact ggcggtatgg atgcggcggg accagagaaa   4740
aatcactcag ggtcaatgcc agcgcttcgt taatacagat gtaggtgttc cacagggtag   4800
ccagcagcat cctgcgatgc agatccggaa cataatggtg cagggcgctg acttccgcgt   4860
ttccagactt tacgaaacac ggaaaccgaa gaccattcat gttgttgctc aggtcgcaga   4920
cgttttgcag cagcagtcgc ttcacgttcg ctcgcgtatc ggtgattcat tctgctaacc   4980
agtaaggcaa ccccgccagc ctagccgggt cctcaacgac aggagcacga tcatgcgcac   5040
ccgtggccag gacccaacgc tgcccgagat gcgccgcgtg cggctgctgg agatggcgga   5100
cgcgatggat atgttctgcc aagggttggt ttgcgcattc acagttctcc gcaagaattg   5160
attggctcca attcttggag tggtgaatcc gttagcgagg tgccgccggc ttccattcag   5220
gtcgaggtgg cccggctcca tgcaccgcga cgcaacgcgg ggaggcagac aaggtatagg   5280
gcggcgccta caatccatgc caacccgttc catgtgctcg ccgaggcggc ataaatcgcc   5340
```

-continued

```
gtgacgatca gcggtccagt gatcgaagtt aggctggtaa gagccgcgag cgatccttga    5400
agctgtccct gatggtcgtc atctacctgc ctggacagca tggcctgcaa cgcgggcatc    5460
ccgatgccgc cggaagcgag aagaatcata atggggaagg ccatccagcc tcgcgtcgcg    5520
aacgccagca agacgtagcc cagcgcgtcg gccgccatgc cggcgataat ggcctgcttc    5580
tcgccgaaac gtttggtggc gggaccagtg acgaaggctt gagcgagggc gtgcaagatt    5640
ccgaataccg caagcgacag gccgatcatc gtcgcgctcc agcgaaagcg gtcctcgccg    5700
aaaatgaccc agagcgctgc cggcacctgt cctacgagtt gcatgataaa gaagacagtc    5760
ataagtgcgg cgacgatagt catgccccgc gcccaccgga aggagctgac tgggttgaag    5820
gctctcaagg gcatcggtcg agatcccggt gcctaatgag tgagctaact tacattaatt    5880
gcgttgcgct cactgcccgc tttccagtcg ggaaacctgt cgtgccagct gcattaatga    5940
atcggccaac gcgcggggag aggcggtttg cgtattgggc gccagggtgg ttttcttttt    6000
caccagtgag acgggcaaca gctgattgcc cttcaccgcc tggccctgag agagttgcag    6060
caagcggtcc acgctggttt gccccagcag gcgaaaatcc tgtttgatgg tggttaacgg    6120
cgggatataa catgagctgt cttcggtatc gtcgtatccc actaccgaga tatccgcacc    6180
aacgcgcagc ccggactcgg taatggcgcg cattgcgccc agcgccatct gatcgttggc    6240
aaccagcatc gcagtgggaa cgatgccctc attcagcatt tgcatggttt gttgaaaacc    6300
ggacatggca ctccagtcgc cttcccgttc cgctatcggc tgaatttgat tgcgagtgag    6360
atatttatgc cagccagcca gacgcagacg cgccgagaca gaacttaatg ggcccgctaa    6420
cagcgcgatt tgctggtgac ccaatgcgac cagatgctcc acgcccagtc gcgtaccgtc    6480
ttcatgggag aaaataatac tgttgatggg tgtctggtca gagacatcaa gaaataacgc    6540
cggaacatta gtgcaggcag cttccacagc aatggcatcc tggtcatcca gcggatagtt    6600
aatgatcagc ccactgacgc gttgcgcgag aagattgtgc accgccgctt tacaggcttc    6660
gacgccgctt cgttctacca tcgacaccac cacgctggca cccagttgat cggcgcgaga    6720
tttaatcgcc gcgacaattt gcgacggcgc gtgcagggcc agactggagg tggcaacgcc    6780
aatcagcaac gactgtttgc ccgccagttg ttgtgccacg cggttgggaa tgtaattcag    6840
ctccgccatc gccgcttcca cttttttcccg cgttttcgca gaaacgtggc tggcctggtt    6900
caccacgcgg gaaacggtct gataagagac accggcatac tctgcgacat cgtataacgt    6960
tactggtttc acattcacca ccctgaattg actctcttcc gggcgctatc atgccatacc    7020
gcgaaaggtt ttgcgccatt cgatggtgtc cgggatctcg acgctctccc ttatgcgact    7080
cctgcattag gaagcagccc agtagtaggt tgaggccgtt gagcaccgcc gccgcaagga    7140
atggtgcatg caaggagatg gcgcccaaca gtccccggc cacggggcct gccaccatac    7200
ccacgccgaa acaagcgctc atgagcccga agtggcgagc ccgatcttcc ccatcggtga    7260
tgtcggcgat ataggcgcca gcaaccgcac ctgtggcgcc ggtgatgccg gccacgatgc    7320
gtccggcgta gaggatcgag atctcgatcc cgcgaaat                            7358
```

<210> SEQ ID NO 7
<211> LENGTH: 4409
<212> TYPE: DNA
<213> ORGANISM: Methylococcus capsulatus

<400> SEQUENCE: 7

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
```

```
tcactcatta ggcacccag gctttacact ttatgcttcc ggctcgtatg ttgtgtggaa    180
ttgtgagcgg ataacaattt cacacaggaa acagctatga ccatgattac gccaagcttg    240
gtaccgagct cggatccact agtaacggcc gccagtgtgc tggaattcgc ccttggagct    300
catccgaaga taagcgcttt ccgcgcagcc cgattctttc atggatcacg attccattga    360
atgcggcgaa agtctcaggg tccggtcatg aatgaagagt tatggcgcc cagtacgtca    420 ccgttatgtc cgatggctgt atcaaacaaa gacacgtgta gtgatatcgg acaactcgtc    480
catccccgtc ggagcattcg gataacgtgc tcatcgttcc aaaatattga tatacggtat    540
acgtatccga agaataaagt tggcacgatc cctgtaacta ggttgtcacg acctcgtcgg    600
aggttgtatg tccggtgttc cgtgacgtca tcggcattc atcattcata gaatgtgtta    660
cggaggaaac aacatatgag agacaccatg aacgaaaagc attgctactc cttactggcc    720
gccggcctca tcgccgccgt gccgcaactc gcagccgccc atggcctgga ttaagggcga    780
attctgcaga tatccatcac actggcggcc gctcgagcat gcatctagag gcccaattc    840 gccctatagt gagtcgtatt acaattcact ggccgtcgtt ttacaacgtc gtgactggga    900
aaaccctggc gttacccaac ttaatcgcct tgcagcacat ccccctttcg ccagctggcg    960
taatagcgaa gaggcccgca ccgatcgccc ttcccaacag ttgcgcagcc tgaatggcga   1020
atggacgcgc cctgtagcgg cgcattaagc gcggcgggtg tggtggttac gcgcagcgtg   1080
accgctacac ttgccagcgc cctagcgccc gctcctttcg ctttcttccc ttcctttctc   1140
gccacgttcg ccggctttcc ccgtcaagct ctaaatcggg ggctccttt agggttccga   1200 tttagtgctt tacggcacct cgaccccaaa aaacttgatt agggtgatgg ttcacgtagt   1260
gggccatcgc cctgatagac ggttttcgc cctttgacgt tggagtccac gttctttaat   1320
agtggactct tgttccaaac tggaacaaca ctcaaccctat ctcggtcta ttcttttgat   1380 ttataaggga ttttgccgat ttcggcctat tggttaaaaa atgagctgat ttaacaaaaa   1440
tttaacgcga atttaacaa aattcagggc gcaagggctg ctaaaggaag cggaacacgt   1500
agaaagccag tccgcagaaa cggtgctgac cccggatgaa tgtcagctac tgggctatct   1560
ggacaaggga aaacgcaagc gcaaagagaa agcaggtagc ttgcagtggg cttacatggc   1620
gatagctaga ctgggcggtt ttatggacag caagcgaacc ggaattgcca gctggggcgc   1680
cctctggtaa ggttgggaag ccctgcaaag taaactggat ggctttcttg ccgccaagga   1740
tctgatggcg caggggatca agatctgatc aagagacagg atgaggatcg tttcgcatga   1800
ttgaacaaga tggattgcac gcaggttctc cggccgcttg ggtggagagg ctattcggct   1860
atgactgggc acaacagaca atcggctgct ctgatgccgc cgtgttccgg ctgtcagcgc   1920
aggggcgccc ggttcttttt gtcaagaccg acctgtccgg tgccctgaat gaactgcagg   1980
acgaggcagc gcggctatcg tggctggcca cgacgggcgt tccttgcgca gctgtgctcg   2040
acgttgtcac tgaagcggga agggactggc tgctattggg cgaagtgccg gggcaggatc   2100
tcctgtcatc ccaccttgct cctgccgaga agtatccat catggctgat gcaatgcggc   2160
ggctgcatac gcttgatccg gctacctgcc cattcgacca caagcgaaa catcgcatcg   2220 agcgagcacg tactcggatg gaagccggtc ttgtcgatca ggatgatctg gacgaagagc   2280 atcagggct cgcgccagcc gaactgttcg ccaggctcaa ggcgcgcatg cccgacggcg   2340
aggatctcgt cgtgacccat ggcgatgcct gcttgccgaa tatcatggtg gaaaatggcc   2400
gcttttctgg attcatcgac tgtggccggc tgggtgtggc ggaccgctat caggacatag   2460
cgttggctac ccgtgatatt gctgaagagc ttggcggcga atgggctgac cgcttcctcg   2520
```

| | |
|---|---:|
| tgctttacgg tatcgccgct cccgattcgc agcgcatcgc cttctatcgc cttcttgacg | 2580 |
| agttcttctg aattgaaaaa ggaagagtat gagtattcaa catttccgtg tcgcccttat | 2640 |
| tcccttttt gcggcatttt gccttcctgt ttttgctcac ccagaaacgc tggtgaaagt | 2700 |
| aaaagatgct gaagatcagt tgggtgcacg agtgggttac atcgaactgg atctcaacag | 2760 |
| cggtaagatc cttgagagtt ttcgccccga agaacgtttt ccaatgatga gcacttttaa | 2820 |
| agttctgcta tgtggcgcgg tattatcccg tattgacgcc gggcaagagc aactcggtcg | 2880 |
| ccgcatacac tattctcaga atgacttggt tgagtactca ccagtcacag aaaagcatct | 2940 |
| tacggatggc atgacagtaa gagaattatg cagtgctgcc ataaccatga gtgataacac | 3000 |
| tgcggccaac ttacttctga caacgatcgg aggaccgaag gagctaaccg ctttttttgca | 3060 |
| caacatgggg gatcatgtaa ctcgccttga tcgttgggaa ccggagctga atgaagccat | 3120 |
| accaaacgac gagcgtgaca ccacgatgcc tgtagcaatg gcaacaacgt tgcgcaaact | 3180 |
| attaactggc gaactactta ctctagcttc ccggcaacaa ttaatagact ggatggaggc | 3240 |
| ggataaagtt gcaggaccac ttctgcgctc ggcccttccg gctggctggt ttattgctga | 3300 |
| taaatctgga gccggtgagc gtgggtctcg cggtatcatt gcagcactgg ggccagatgg | 3360 |
| taagccctcc cgtatcgtag ttatctacac gacggggagt caggcaacta tggatgaacg | 3420 |
| aaatagacag atcgctgaga taggtgcctc actgattaag cattggtaac tgtcagacca | 3480 |
| agtttactca tatatacttt agattgattt aaaacttcat ttttaattta aaaggatcta | 3540 |
| ggtgaagatc cttttgata atctcatgac caaaatccct taacgtgagt tttcgttcca | 3600 |
| ctgagcgtca gaccccgtag aaaagatcaa aggatcttct tgagatcctt ttttctgcg | 3660 |
| cgtaatctgc tgcttgcaaa caaaaaaacc accgctacca gcggtggttt gtttgccgga | 3720 |
| tcaagagcta ccaactcttt ttccgaaggt aactggcttc agcagagcgc agataccaaa | 3780 |
| tactgttctt ctagtgtagc cgtagttagg ccaccacttc aagaactctg tagcaccgcc | 3840 |
| tacatacctc gctctgctaa tcctgttacc agtggctgct gccagtggcg ataagtcgtg | 3900 |
| tcttaccggg ttggactcaa gacgatagtt accggataag gcgcagcggt cgggctgaac | 3960 |
| ggggggttcg tgcacacagc ccagcttgga gcgaacgacc tacaccgaac tgagatacct | 4020 |
| acagcgtgag ctatgagaaa gcgccacgct tcccgaaggg agaaaggcgg acaggtatcc | 4080 |
| ggtaagcggc agggtcggaa caggagagcg cacgagggag cttccagggg gaaacgcctg | 4140 |
| gtatctttat agtcctgtcg ggtttcgcca cctctgactt gagcgtcgat ttttgtgatg | 4200 |
| ctcgtcaggg gggcggagcc tatggaaaaa cgccagcaac gcggcctttt tacggttcct | 4260 |
| ggccttttgc tggccttttg ctcacatgtt ctttcctgcg ttatcccctg attctgtgga | 4320 |
| taaccgtatt accgcctttg agtgagctga taccgctcgc cgcagccgaa cgaccgagcg | 4380 |
| cagcgagtca gtgagcgagg aagcggaag | 4409 |

<210> SEQ ID NO 8
<211> LENGTH: 5132
<212> TYPE: DNA
<213> ORGANISM: Methylococcus capsulatus

<400> SEQUENCE: 8

| | |
|---|---:|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |

```
gtaccgagct cggatccact agtaacggcc gccagtgtgc tggaattcgc ccgcagccgc    300
ccatggcctg gacacgctgg accgggacgg cgacggctcc acggccgacg ccgattgcaa    360
cgacttcgcg cccaccatcc atccgggcgc cgccgaagcg acgctggacg gcgtggattc    420
caactgcgac gggcgcgact ccggcgtggc ggaagtcgtc gagaccttca agaatccggg    480
cacctactcc agcccggtca tcaacttcaa gatcgcttcg ccgccggggc cgggaacgcc    540
catctacggg ccgccgcgtg atttctccgg ttacaacaag agctactcgc tggcgatcgg    600
caagacctcg tactacgatc cgaccaccgg caccaagtgg aacgacgaca ccatcacgcc    660
ggtcagtgat ggtcaggaca tctggcgcgg ctggacccat accggcaagt ggtcgttctt    720
caacggcaag gccggcgaca agatcaccct cagcgtacag cgtgatgcgc aggaagccag    780
cctgaaaggc gcccatccgg gcttcatcct gttctggcgg cccgagggcg gtccgctgtt    840
ctgggccggc acccaggatc tcgacgaggg ccagaccgcg ctgcccgccg actccgacac    900
cgttatcggc cacgtgatcg ttcagcacgc cgactggacc ctgcagggct tgccgcccaa    960
ggccgaccat accgcacccg cgggcgtgga taccgagctc tatcccatga agccggacag    1020
ctacaccatg tactacgtcg actccggcta cgatgccgac aagtacgtgg catcgaagaa    1080
gctcatcatg caccccacgg cgttcaaagg gctggccctg aacgacggca ccgccggggc    1140
gttcaccaag tccatcaccc tgccgaagac gggctattac atgctgtacg tcgccaacgt    1200
cctggaagtg gacgactgga gcgtcgacgc ggacggcaag ctcaccacca ccggcgaagt    1260
ctgggaagtg ccgccaagg gctgctgggt caacatcacg atctccaagc cgtaaatccg    1320
gcttgatgtg cgtgatcctt cggagcggcc agtcgaccgt tccgcgggga aaacttccgg    1380
agccaatccc cgtcctctgc ggcggggatt tttttattcg gcggaaccga gttgggcgac    1440 ggcttttttcc agcttcttca accggctcca gatttcgtgc aggctcgagg gggttaaggg    1500
cgaattctgc agatatccat cacactggcg gccgctcgag catgcatcta gagggcccaa    1560
ttcgccctat agtgagtcgt attacaattc actggccgtc gttttacaac gtcgtgactg    1620
ggaaaaccct ggcgttaccc aacttaatcg ccttgcagca catccccctt tcgccagctg    1680
gcgtaatagc gaagaggccc gcaccgatcg cccttcccaa cagttgcgca gcctgaatgg    1740
cgaatggacg cgccctgtag cggcgcatta agcgcggcgg gtgtggtggt tacgcgcagc    1800
gtgaccgcta cacttgccag cgccctagcg cccgctcctt tcgctttctt cccttccttt    1860
ctcgccacgt tcgccggctt tccccgtcaa gctctaaatc gggggctccc tttagggttc    1920
cgatttagtg ctttacggca cctcgacccc aaaaaacttg attagggtga tggttcacgt    1980
agtgggccat cgccctgata gacggttttt cgccctttga cgttggagtc acgttctttt    2040
aatagtggac tcttgttcca aactggaaca acactcaacc ctatctcggt ctattctttt    2100
gatttataag ggattttgcc gatttcggcc tattggttaa aaaatgagct gatttaacaa    2160
aaatttaacg cgaattttaa caaaattcag ggcgcaaggg ctgctaaagg aagcggaaca    2220
cgtagaaagc cagtccgcag aaacggtgct gaccccggat gaatgtcagc tactgggcta    2280
tctggacaag ggaaaacgca agcgcaaaga gaaagcaggt agcttgcagt gggcttacat    2340
ggcgatagct agactgggcg gttttatgga cagcaagcga accggaattg ccagctgggg    2400
cgccctctgg taaggttggg aagccctgca agtaaactg gatggctttc ttgccgccaa    2460
ggatctgatg gcgcagggga tcaagatctg atcaagagac aggatgagga tcgtttcgca    2520
tgattgaaca agatggattg cacgcaggtt ctccggccgc ttgggtggag aggctattcg    2580
gctatgactg ggcacaacag acaatcggct gctctgatgc cgccgtgttc cggctgtcag    2640
```

```
cgcaggggcg cccggttctt tttgtcaaga ccgacctgtc cggtgccctg aatgaactgc   2700
aggacgaggc agcgcggcta tcgtggctgg ccacgacggg cgttccttgc gcagctgtgc   2760
tcgacgttgt cactgaagcg ggaagggact ggctgctatt gggcgaagtg ccggggcagg   2820
atctcctgtc atcccacctt gctcctgccg agaaagtatc catcatggct gatgcaatgc   2880
ggcggctgca tacgcttgat ccggctacct gcccattcga ccaccaagcg aaacatcgca   2940
tcgagcgagc acgtactcgg atggaagccg gtcttgtcga tcaggatgat ctggacgaag   3000
agcatcaggg gctcgcgcca gccgaactgt tcgccaggct caaggcgcgc atgcccgacg   3060
gcgaggatct cgtcgtgacc catggcgatg cctgcttgcc gaatatcatg gtggaaaatg   3120
gccgcttttc tggattcatc gactgtggcc ggctgggtgt ggcggaccgc tatcaggaca   3180
tagcgttggc tacccgtgat attgctgaag agcttggcgg cgaatgggct gaccgcttcc   3240
tcgtgcttta cggtatcgcc gctcccgatt cgcagcgcat cgccttctat cgccttcttg   3300
acgagttctt ctgaattgaa aaaggaagag tatgagtatt caacatttcc gtgtcgccct   3360
tattcccttt tttgcggcat tttgccttcc tgttttttgct cacccagaaa cgctggtgaa   3420
agtaaaagat gctgaagatc agttgggtgc acgagtgggt tacatcgaac tggatctcaa   3480
cagcggtaag atccttgaga gttttcgccc cgaagaacgt tttccaatga tgagcacttt   3540
taaagttctg ctatgtggcg cggtattatc ccgtattgac gccgggcaag agcaactcgg   3600
tcgccgcata cactattctc agaatgactt ggttgagtac tcaccagtca cagaaaagca   3660
tcttacggat ggcatgacag taagagaatt atgcagtgct gccataacca tgagtgataa   3720
cactgcggcc aacttacttc tgacaacgat cggaggaccg aaggagctaa ccgcttttttt   3780 gcacaacatg ggggatcatg taactcgcct tgatcgttgg gaaccggagc tgaatgaagc   3840
cataccaaac gacgagcgtg acaccacgat gcctgtagca atggcaacaa cgttgcgcaa   3900
actattaact ggcgaactac ttactctagc ttcccggcaa caattaatag actggatgga   3960
ggcggataaa gttgcaggac cacttctgcg ctcggccctt ccggctggct ggtttattgc   4020
tgataaatct ggagccggtg agcgtgggtc tcgcggtatc attgcagcac tggggccaga   4080
tggtaagccc tcccgtatcg tagttatcta cacgacgggg agtcaggcaa ctatggatga   4140
acgaaataga cagatcgctg agataggtgc ctcactgatt aagcattggt aactgtcaga   4200
ccaagtttac tcatatatac tttagattga tttaaaactt catttttaat ttaaaaggat   4260
ctaggtgaag atcctttttg ataatctcat gaccaaaatc ccttaacgtg agttttcgtt   4320
ccactgagcg tcagaccccg tagaaaagat caaaggatct tcttgagatc ctttttttct   4380
gcgcgtaatc tgctgcttgc aaacaaaaaa accaccgcta ccagcggtgg tttgtttgcc   4440
ggatcaagag ctaccaactc tttttccgaa ggtaactggc ttcagcagag cgcagatacc   4500
aaatactgtt cttctagtgt agccgtagtt aggccaccac ttcaagaact ctgtagcacc   4560
gcctacatac ctcgctctgc taatcctgtt accagtggct gctgccagtg gcgataagtc   4620
gtgtcttacc gggttggact caagacgata gttaccggat aaggcgcagc ggtcgggctg   4680
aacggggggt tcgtgcacac agcccagctt ggagcgaacg acctacaccg aactgagata   4740
cctacagcgt gagctatgag aaagcgccac gcttcccgaa gggagaaagg cggacaggta   4800
tccggtaagc ggcagggtcg gaacaggaga gcgcacgagg gagcttccag ggggaaacgc   4860
ctggtatctt tatagtcctg tcgggtttcg ccacctctga cttgagcgtc gatttttgtg   4920
atgctcgtca gggggggcgga gcctatggaa aaacgccagc aacgcggcct ttttacggtt   4980
cctggccttt tgctggcctt tgctcacat gttctttcct gcgttatccc ctgattctgt   5040
```

```
ggataaccgt attaccgcct ttgagtgagc tgataccgct cgccgcagcc gaacgaccga   5100
gcgcagcgag tcagtgagcg aggaagcgga ag                                5132

<210> SEQ ID NO 9
<211> LENGTH: 7138
<212> TYPE: DNA
<213> ORGANISM: Methylococcus capsulatus

<400> SEQUENCE: 9
ccggtaaacc agcaatagac ataagcggct atttaacgac cctgccctga accgacgacc     60
gggtcgaatt tgctttcgaa tttctgccat tcatccgctt attatcactt attcaggcgt    120
agcaccaggc gtttaagggc accataact gccttaaaaa aattacgccc cgccctgcca    180
ctcatcgcag tcggcctatt ggttaaaaaa tgagctgatt taacaaaaat ttaacgcgaa    240
ttttaacaaa atattaacgc ttacaatttc cattcgccat tcaggctgcg caactgttgg    300
gaagggcgat cggtgcgggc ctcttcgcta ttacgccagc tggcgaaagg gggatgtgct    360
gcaaggcgat taagttgggt aacgccaggg ttttcccagt cacgacgttg taaaacgacg    420
gccagtgagc gcgcgtaata cgactcacta tagggcgaat tggagctcca ccgcggtggc    480
ggccgctcta gatgcatgct cgagcggccg ccagtgtgat ggatatctgc agaattcgcc    540
cttaagagct catccgaaga taagcgcttt ccgcgcagcc cgattctttc atggatcacg    600
attccattga atgcggcgaa agtctcaggg tccggtcatg aatgaagagt tatggcggcc    660
cagtacgtca ccgttatgtc cgatggctgt atcaaacaaa gacacgtgta gtgatatcgg    720
acaactcgtc catccccgtc ggagcattcg ataacgtgc tcatcgttcc aaaatattga    780
tatacggtat acgtatccga agaataaagt tggcacgatc cctgtaacta ggttgtcacg    840
acctcgtcgg aggttgtatg tccggtgttc cgtgacgtca tcgggcattc atcattcata    900
gaatgtgtta cggaggaaac aacatatgag agacaccatg aacgaaaagc attgctactc    960
cttactggcc gccggcctca tcgccgccgt gccgcaactc gcagccgccc atggcctgga   1020
cacgctggac cgggacggcg acggctccac ggccgacgcc gattgcaacg acttcgcgcc   1080
caccatccat ccgggcgccg ccgaagcgac gctggacggc gtggattcca actgcgacgg   1140
gcgcgactcc ggcgtggcgg aagtcgtcga gaccttcaag aatccgggca cctactccag   1200
cccggtcatc aacttcaaga tcgcttcgcc gccggggccg ggaacgccca tctacgggcc   1260
gccgcgtgat ttctccggtt acaacaagag ctactgctg gcgatcggca agacctcgta   1320
ctacgatccg accaccggca ccaagtggaa cgacgacacc atcacgccgg tcagtgatgg   1380
tcaggacatc tggcgcggct ggaccccatac cggcaagtgg tcgttcttca cggcaaggc   1440 cggcgacaag atcaccctca gcgtacagcg tgatgcgcag gaagccagcc tgaaaggcgc   1500
ccatccgggc ttcatcctgt tctggcggcc cgagggcgt ccgctgttct gggccggcac   1560
ccaggatctc gacgagggcc agaccgcgct gcccgccgac tccgacaccg ttatcggcca   1620
cgtgatcgtt cagcacgccg actggaccct gcagggcttg ccgcccaagg ccgaccatac   1680
cgcacccgcg ggcgtggata ccgagctcta tcccatgaag ccggacagct acaccatgta   1740
ctacgtcgac tccggctacg atgccgacaa gtacgtggca tcgaagaagc tcatcatgca   1800
ccccacggcg ttcaaaggc tggccctgaa cgacggcacc gccggggcgt tcaccaagtc   1860
catcaccctg ccgaagacgg gctattacat gctgtacgtc gccaacgtcc tggaagtgga   1920
cgactggagc gtcgacgcgg acggcaagct caccaccacc ggcgaagtct gggaagtgcc   1980
ggccaagggc tgctgggtca acatcacgat ctccaagccg taaatccggc ttgatgtgcg   2040
```

```
tgatccttcg gagcggccag tcgaccgttc cgcggggaaa acttccggag ccaatccccg    2100
tcctctgcgg cggggatttt tttattcggc ggaaccgagt tgggcgacgg cttttttccag   2160 cttcttcaac cggctccaga tttcgtgcag gctcgagggg cgaattccag cacactggcg    2220
gccgttacta gtggatccgg ctgctaacaa agcccgaaag gaagctgagt tggctgctgc    2280
caccgctgag caataactag cataacccct tggggcctct aaacgggtct tgagggggttt  2340 tttgctgaaa ggaggaacta tatccggata tcccgcaaga ggcccggcag taccggcata    2400
accaagccta tgcctacagc atccagggtg acggtgccga ggatgacgat gagcgcattg    2460
ttagatttca tacacggtgc ctgactgcgt tagcaattta actgtgataa actaccgcat    2520
taaagcttat cgataccgtc gacctcgagg ggggcccgg tacccagctt ttgttccctt     2580
tagtgagggt taattgcgcg cttggcgtaa tcatggtcat agctgtttcc tgtgtgaaat    2640
tgttatccgc tcacaattcc acacaacata cgagccggaa gcataaagtg taaagcctgg    2700
ggtgcctaat gagtgagcta actcacatta attgcgttgc gctcactgcc cgcttttccag  2760 tcgggaaacc tgtcgtgcca gctgcattaa tgaatcggcc aacgcgcggg gagaggcggt    2820
ttgcgtattg ggcgcatgca taaaaactgt tgtaattcat taagcattct gccgacatgg    2880
aagccatcac aaacggcatg atgaacctga atcgccagcg gcatcagcac cttgtcgcct    2940
tgcgtataat atttgcccat ggggggtgggc gaagaactcc agcatgagat ccccgcgctg   3000
gaggatcatc cagccggcgt cccggaaaac gattccgaag cccaacctttt catagaaggc   3060 ggcggtggaa tcgaaatctc gtgatggcag gttgggcgtc gcttggtcgg tcatttcgaa    3120
ccccagagtc ccgctcagaa gaactcgtca agaaggcgat agaaggcgat gcgctgcgaa    3180
tcgggagcgg cgataccgta aagcacgagg aagcggtcag cccattcgcc gccaagctct    3240
tcagcaatat cacgggtagc caacgctatg tcctgatagc ggtccgccac acccagccgg    3300
ccacagtcga tgaatccaga aaagcggcca ttttccacca tgatattcgg caagcaggca    3360
tcgccatggg tcacgacgag atcctcgccg tcgggcatgc gcgccttgag cctggcgaac    3420
agttcggctg cgcgagccc ctgatgctct tcgtccagat catcctgatc gacaagaccg     3480
gcttccatcc gagtacgtgc tcgctcgatg cgatgtttcg cttggtggtc gaatgggcag    3540
gtagccggat caagcgtatg cagccgccgc attgcatcag ccatgatgga tactttctcg    3600
gcaggagcaa ggtgagatga caggagatcc tgccccggca cttcgcccaa tagcagccag    3660
tcccttcccg cttcagtgac aacgtcgagc acagctgcgc aaggaacgcc cgtcgtggcc    3720
agccacgata gccgcgctgc ctcgtcctgc agttcattca gggcaccgga caggtcggtc    3780
ttgacaaaaa gaaccgggcg cccctgcgct gacagccgga acacggcggc atcagagcag    3840
ccgattgtct gttgtgccca gtcatagccg aatagcctct ccacccaagc ggccggagaa    3900
cctgcgtgca atccatcttg ttcaatcatg cgaaacgatc ctcatcctgt ctcttgatca    3960
gatcttgatc ccctgcgcca tcagatcctt ggcggcaaga aagccatcca gtttactttg    4020
cagggcttcc caaccttacc agagggcgcc ccagctggca attccggttc gcttgctgtc    4080
cataaaaccg cccagtctag ctatcgccat gtaagcccac tgcaagctac ctgctttctc    4140
tttgcgcttg cgttttccct tgtccagata gcccagtagc tgacattcat cccaggtggc    4200
acttttcggg gaaatgtgcg cgcccgcgtt cctgctggcg ctgggcctgt ttctggcgct    4260
ggacttcccg ctgttccgtc agcagctttt cgcccacggc cttgatgatc gcggcggcct    4320
tggcctgcat atcccgattc aacgccccca gggcgtccag aacgggcttc aggcgctccc    4380
gaaggtctcg ggccgtctct tgggcttgat cggccttctt gcgcatctca cgcgctcctg    4440
```

```
cggcggcctg tagggcaggc tcatacccct gccgaaccgc ttttgtcagc cggtcggcca    4500
cggcttccgg cgtctcaacg cgctttgaga ttcccagctt ttcggccaat ccctgcggtg    4560
cataggcgcg tggctcgacc gcttgcgggc tgatggtgac gtggcccact ggtggccgct    4620
ccagggcctc gtagaacgcc tgaatgcgcg tgtgacgtgc cttgctgccc tcgatgcccc    4680
gttgcagccc tagatcggcc acagcggccg caaacgtggt ctggtcgcgg gtcatctgcg    4740 cttgttgcc gatgaactcc ttggccgaca gcctgccgtc ctgcgtcagc ggcaccacga    4800
acgcggtcat gtgcgggctg gtttcgtcac ggtggatgct ggccgtcacg atgcgatccg    4860
ccccgtactt gtccgccagc cacttgtgcg ccttctcgaa gaacgccgcc tgctgttctt    4920
ggctggccga cttccaccat tccgggctgg ccgtcatgac gtactcgacc gccaacacag    4980
cgtccttgcg ccgcttctct ggcagcaact cgcgcagtcg gcccatcgct tcatcggtgc    5040
tgctggccgc ccagtgctcg ttctctggcg tcctgctggc gtcagcgttg ggcgtctcgc    5100
gctcgcggta ggcgtgcttg agactggccg ccacgttgcc cattttcgcc agcttcttgc    5160
atcgcatgat cgcgtatgcc gccatgcctg cccctccctt ttggtgtcca accggctcga    5220 cggggggcagc gcaaggcggt gcctccgcg ggccactcaa tgcttgagta tactcactag    5280
actttgcttc gcaaagtcgt gaccgcctac ggcggctgcg gcgccctacg ggcttgctct    5340
ccgggcttcg ccctgcgcgg tcgctgcgct cccttgccag cccgtggata tgtgacgat    5400 ggccgcgagc ggccaccggc tggctcgctt cgctcggccc gtggacaacc ctgctggaca    5460
agctgatgga caggctgcgc ctgcccacga gcttgaccac agggattgcc caccggctac    5520
ccagccttcg accacatacc caccggctcc aactgcgcgg cctgcggcct tgccccatca    5580 attttttaa ttttctctgg ggaaaagcct ccggcctgcg gcctgcgcgc ttcgcttgcc    5640
ggttggacac caagtggaag gcgggtcaag gctcgcgcag cgaccgcgca gcggcttggc    5700
cttgacgcgc ctggaacgac ccaagccat gcgagtgggg gcagtcgaag gcgaagcccg    5760
cccgcctgcc ccccgagcct cacggcggcg agtgcggggg ttccaagggg gcagcgccac    5820
cttgggcaag gccgaaggcc gcgcagtcga tcaacaagcc ccggaggggc cacttttgc    5880 cggagggga gccgcgccga aggcgtgggg gaaccccgca ggggtgccct tctttgggca    5940
ccaaagaact agatatag gg cgaaatgcga aagacttaaa aatcaacaac ttaaaaagg    6000 ggggtacgca acagctcatt gcggcacccc ccgcaatagc tcattgcgta ggttaaagaa    6060
aatctgtaat tgactgccac ttttacgcaa cgcataattg ttgtcgcgct gccgaaaagt    6120
tgcagctgat tgcgcatggt gccgcaaccg tgcggcaccc taccgcatgg agataagcat    6180
ggccacgcag tccagagaaa tcggcattca agccaagaac aagcccggtc actgggtgca    6240
aacggaacgc aaagcgcatg aggcgtgggc cgggcttatt gcgaggaaac ccacggcggc    6300
aatgctgctg catcacctcg tggcgcagat gggccaccag aacgccgtgg tggtcagcca    6360
gaagacactt tccaagctca tcggacgttc tttgcggacg gtccaatacg cagtcaagga    6420
cttggtggcc gagcgctgga tctccgtcgt gaagctcaac ggccccggca ccgtgtcggc    6480
ctacgtggtc aatgaccgcg tggcgtgggg ccagccccgc gaccagttgc gcctgtcggt    6540
gttcagtgcc gccgtggtgg ttgatcacga cgaccaggac gaatcgctgt tgggcatgg    6600 cgacctgcgc cgcatcccga ccctgtatcc gggcgagcag caactaccga ccggcccgg    6660 cgaggagccg cccagccagc ccggcattcc gggcatggaa ccagacctgc cagccttgac    6720
cgaaacggag gaatgggaac ggcgcgggca gcagcgcctg ccgatgcccg atgagccgtg    6780
ttttctggac gatggcgagc cgttggagcc gccgacacgg gtcacgctgc cgcgccggta    6840
```

```
gcacttgggt tgcgcagcaa cccgtaagtg cgctgttcca gactatcggc tgtagccgcc   6900
tcgccgccct ataccttgtc tgcctcsccg cgttgcgtcg cggtgcatgg agccgggcca   6960
cctcgacctg aatggaagcc ggcggcacct cgctaacgga ttcaccgttt ttatcaggct   7020
ctgggaggca gaataaatga tcatatcgtc aattattacc tccacgggga gagcctgagc   7080
aaactggcct caggcatttg agaagcacac ggtcacactg cttccggtag tcaataaa    7138
```

```
<210> SEQ ID NO 10
<211> LENGTH: 2940
<212> TYPE: DNA
<213> ORGANISM: Methylococcus capsulatus

<400> SEQUENCE: 10
```

```
caaaatatta acgcttacaa tttccattcg ccattcaggc tgcgcaactg ttgggaaggg     60
cgatcggtgc gggcctcttc gctattacgc cagctggcga aaggggatg tgctgcaagg    120 cgattaagtt gggtaacgcc agggttttcc cagtcacgac gttgtaaaac gacggccagt    180
gagcgcgcgt aatacgactc actatagggc gaattggagc tcttaattaa tttccgcgca    240
gcccgattct ttcatggatc acgattccat gaatgcggc gaaatgtctc agggtccggt    300
cttgaatgaa gagttatggc ggcccagtac gtcaccgtta tgtccgatgg ctgtatcaaa    360
caaagacacg tgtagtgata tcggacaact cgtccatccc cgtcgggagc attcggataa    420
tcgtgtcatc gttccaaaat attgatatat cggtatacgt atccgaagaa taaagttggc    480
acgatccctg taactaggtt gtcacgacct cgtcggaggt gtatgtccg gtgttccgtg    540 acgtcatcgg gcattcatca ttcatagaat gtgttacgga ggaaacaaca tatgagagac    600
accatgaacg aaaagcattg ctactcctta ctggccgccg gcctcatcgc cgccgtgccg    660
caactcgcag ccgcccatgg taagaaattg gctaaaccag cgaccacaaa ggccgttaat    720
ccccagcccc gtcgacgcaa caacaaccgt cggcgtggca tgagagcgga tgcacccttta   780 gctaaggcct cgactatcac gggatttgga cgtgggacca atgacgtcca tctcacgggt    840
atgtcgagaa tcgcccaagc ggttatccca gctggcaccg gcacggacgg atacatcgtg    900
gttgacgaaa ccatcgtccc cgagctcttg ccaagactgg gatttgctgc tagaatcttc    960
cagcgatacg ctgttgagac actggagttc gaaattcagc caatgtgccc cgcaaacacg   1020
ggcggtggtt acgtggctgg cttcctgcct gatccaactg acagcgacca caccttcgac   1080
gcaattcaag cgactcgcgg tgcggtcgtt gccaaatggt gggaaagcag aacaatccga   1140
ccccagcatg cccgcgcact cctctggacc tcggtcggga aggagcagcg tttgacatcc   1200
ccgggccggt tggtactcct gtgtgccggc aacaacactg acgtcgtcaa cgtgtcagtg   1260
ctgtgtcgct ggagtgtacg tctcagtgtt ccatctctcg agacacctga agatacattc   1320
gctccaatcc taaccctggg accactctac aacgactccc ttgcacccaa cgatttcaaa   1380
tcaatacttc ttggctctac ccagcttgac atcgcccctg acggagccgt ctattcatta   1440
gatcggccgc tgtccattga ctacagtctg ggcactggtg atgtcgaccg tgccgtttac   1500
tggcatgtga agaaagttgc tggcaatgcg ggaacacctg cggggtggtt ccactggggg   1560
ctatgggata atttcaacaa aacattcaca cagggcgctg cctactattc tgatgcgcag   1620
cctcgacaga tcttgctgcc agtgggcacg ctcaacaccc gagctgactc ccatggcctg   1680
gacacgctgg accgggacgg cgacggctcc acggccgacg ccgattgcaa cgacttcgcg   1740
cccaccatcc atccgggcgc cgccgaagcg acgctggacg gcgtggattc caactgcgac   1800
gggcgcgact ccggcgtggc ggaagtcgtc gagaccttca agaatccggg cacctactcc   1860
```

```
agcccggtca tcaacttcaa gatcgcttcg ccgccggggc cgggaacgcc catctacggg    1920
ccgccgcgtg atttctccgg ttacaacaag agctactcgc tggcgatcgg caagacctcg    1980
tactacgatc cgaccaccgg caccaagtgg aacgacgaca ccatcacgcc ggtcagtgat    2040
ggtcaggaca tctggcgcgg ctggacccat accggcaagt ggtcgttctt caacggcaag    2100
gccggcgaca agatcaccct cagcgtacag cgtgatgcgc aggaagccag cctgaaaggc    2160
gcccatccgg gcttcatcct gttctggcgg cccgagggcg gtccgctgtt ctgggccggc    2220
acccaggatc tcgacgaggg ccagaccgcg ctgcccgccg actccgacac cgttatcggc    2280
cacgtgatcg ttcagcacgc cgactggacc ctgcagggct gccgcccaa ggccgaccat    2340 accgcacccg cgggcgtgga taccgagctc tatcccatga agccggacag ctacaccatg    2400
tactacgtcg actccggcta cgatgccgac aagtacgtgg catcgaagaa gctcatcatg    2460
caccccacgg cgttcaaagg gctggccctg aacgacggca ccgccggggc gttcaccaag    2520
tccatcaccc tgccgaagac gggctattac atgctgtacg tcgccaacgt cctggaagtg    2580
gacgactgga gcgtcgacgc ggacggcaag ctcaccacca ccggcgaagt ctgggaagtg    2640
ccggccaagg gctgctgggt caacatcacg atctccaagc cgtaaatccg gcttgatgtg    2700
cgtgatcctt cggagcggcc agtcgaccgt ccgcgggga aaacttccgg agccaatccc    2760
cgtcctctgc ggcggggatt tttttattcg gcggaaccga gttgggcgac ggcttttttcc    2820 agcttcttca accggctcca gatttcgtgc aggctcgagg ggggggcccgg tacccagctt    2880 ttgttcccctt tagtgagggt taattgcgcg cttggcgtaa tcatggtcat agctgtttcc    2940
```

<210> SEQ ID NO 11
<211> LENGTH: 669
<212> TYPE: PRT
<213> ORGANISM: Methylococcus capsulatus

<400> SEQUENCE: 11

```
Lys Lys Leu Ala Lys Pro Ala Thr Thr Lys Ala Val Asn Pro Gln Pro
1               5                   10                  15

Arg Arg Arg Asn Asn Asn Arg Arg Gly Met Arg Ala Asp Ala Pro
            20                  25                  30

Leu Ala Lys Ala Ser Thr Ile Thr Gly Phe Gly Arg Gly Thr Asn Asp
        35                  40                  45

Val His Leu Thr Gly Met Ser Arg Ile Ala Gln Ala Val Ile Pro Ala
    50                  55                  60

Gly Thr Gly Thr Asp Gly Tyr Ile Val Val Asp Glu Thr Ile Val Pro
65                  70                  75                  80

Glu Leu Leu Pro Arg Leu Gly Phe Ala Ala Arg Ile Phe Gln Arg Tyr
                85                  90                  95

Ala Val Glu Thr Leu Glu Phe Glu Ile Gln Pro Met Cys Pro Ala Asn
            100                 105                 110

Thr Gly Gly Gly Tyr Val Ala Gly Phe Leu Pro Asp Pro Thr Asp Ser
        115                 120                 125

Asp His Thr Phe Asp Ala Ile Gln Ala Thr Arg Gly Ala Val Val Ala
    130                 135                 140

Lys Trp Trp Glu Ser Arg Thr Ile Arg Pro Gln His Ala Arg Ala Leu
145                 150                 155                 160

Leu Trp Thr Ser Val Gly Lys Glu Gln Arg Leu Thr Ser Pro Gly Arg
                165                 170                 175

Leu Val Leu Leu Cys Ala Gly Asn Asn Thr Asp Val Val Asn Val Ser
            180                 185                 190
```

Val Leu Cys Arg Trp Ser Val Arg Leu Ser Val Pro Ser Leu Glu Thr
        195                 200                 205

Pro Glu Asp Thr Phe Ala Pro Ile Leu Thr Leu Gly Pro Leu Tyr Asn
210                 215                 220

Asp Ser Leu Ala Pro Asn Asp Phe Lys Ser Ile Leu Leu Gly Ser Thr
225                 230                 235                 240

Gln Leu Asp Ile Ala Pro Asp Gly Ala Val Tyr Ser Leu Asp Arg Pro
            245                 250                 255

Leu Ser Ile Asp Tyr Ser Leu Gly Thr Gly Asp Val Asp Arg Ala Val
        260                 265                 270

Tyr Trp His Val Lys Lys Val Ala Gly Asn Ala Gly Thr Pro Ala Gly
    275                 280                 285

Trp Phe His Trp Gly Leu Trp Asp Asn Phe Asn Lys Thr Phe Thr Gln
290                 295                 300

Gly Ala Ala Tyr Tyr Ser Asp Ala Gln Pro Arg Gln Ile Leu Leu Pro
305                 310                 315                 320

Val Gly Thr Leu Phe Thr Arg Ala Asp Ser Gly Asn His Gly Leu Asp
            325                 330                 335

Thr Leu Asp Arg Asp Gly Asp Gly Ser Thr Ala Asp Ala Asp Cys Asn
        340                 345                 350

Asp Phe Ala Pro Thr Ile His Pro Gly Ala Ala Glu Ala Thr Leu Asp
    355                 360                 365

Gly Val Asp Ser Asn Cys Asp Gly Arg Asp Ser Gly Val Ala Glu Val
370                 375                 380

Val Glu Thr Phe Lys Asn Pro Gly Thr Tyr Ser Ser Pro Val Ile Asn
385                 390                 395                 400

Phe Lys Ile Ala Ser Pro Pro Gly Pro Gly Thr Pro Ile Tyr Gly Pro
            405                 410                 415

Pro Arg Asp Phe Ser Gly Tyr Asn Lys Ser Tyr Ser Leu Ala Ile Gly
        420                 425                 430

Lys Thr Ser Tyr Tyr Asp Pro Thr Thr Gly Thr Lys Trp Asn Asp Asp
    435                 440                 445

Thr Ile Thr Pro Val Ser Asp Gly Gln Asp Ile Trp Arg Gly Trp Thr
450                 455                 460

His Thr Gly Lys Trp Ser Phe Phe Asn Gly Lys Ala Gly Asp Lys Ile
465                 470                 475                 480

Thr Leu Ser Val Gln Arg Asp Ala Gln Glu Ala Ser Leu Lys Gly Ala
            485                 490                 495

His Pro Gly Phe Ile Leu Phe Trp Arg Pro Glu Gly Gly Pro Leu Phe
        500                 505                 510

Trp Ala Gly Thr Gln Asp Leu Asp Glu Gly Gln Thr Ala Leu Pro Ala
    515                 520                 525

Asp Ser Asp Thr Val Ile Gly His Val Ile Val Gln His Ala Asp Trp
530                 535                 540

Thr Leu Gln Gly Leu Pro Pro Lys Ala Asp His Thr Ala Pro Ala Gly
545                 550                 555                 560

Val Asp Thr Glu Leu Tyr Pro Met Lys Pro Asp Ser Tyr Thr Met Tyr
            565                 570                 575

Tyr Val Asp Ser Gly Tyr Asp Ala Asp Lys Tyr Val Ala Ser Lys Lys
        580                 585                 590

Leu Ile Met His Pro Thr Ala Phe Lys Gly Leu Ala Leu Asn Asp Gly
    595                 600                 605

Thr Ala Gly Ala Phe Thr Lys Ser Ile Thr Leu Pro Lys Thr Gly Tyr

```
                    610                 615                 620
Tyr Met Leu Tyr Val Ala Asn Val Leu Glu Val Asp Asp Trp Ser Val
625                 630                 635                 640

Asp Ala Asp Gly Lys Leu Thr Thr Thr Gly Glu Val Trp Glu Val Pro
                645                 650                 655

Ala Lys Gly Cys Trp Val Asn Ile Thr Ile Ser Lys Pro
                660                 665

<210> SEQ ID NO 12
<211> LENGTH: 2299
<212> TYPE: DNA
<213> ORGANISM: Methylococcus capsulatus

<400> SEQUENCE: 12
caaaatatta acgcttacaa tttccattcg ccattcaggc tgcgcaactg ttgggaaggg      60
cgatcggtgc gggcctcttc gctattacgc cagctggcga aaggggatg tgctgcaagg     120 cgattaagtt gggtaacgcc agggttttcc cagtcacgac gttgtaaaac gacggccagt    180
gagcgcgcgt aatacgactc actatagggc gaattggagc tcttaattaa tttccgcgca    240
gcccgattct ttcatggatc acgattccat gaatgcggc gaaatgtctc agggtccggt     300
cttgaatgaa gagttatggc ggcccagtac gtcaccgtta tgtccgatgg ctgtatcaaa    360
caaagacacg tgtagtgata tcggacaact cgtccatccc gtcgggagc attcggataa     420 tcgtgtcatc gttccaaaat attgatatat cggtatacgt atccgaagaa taaagttggc    480
acgatccctg taactaggtt gtcacgacct cgtcggaggt gtatgtccg gtgttccgtg     540 acgtcatcgg gcattcatca ttcatagaat gtgttacgga ggaaacaaca tatgagagac    600
accatgaacg aaaagcattg ctactcctta ctggccgccg gcctcatcgc cgccgtgccg    660
caactcgcag ccgcccatgg cctggacacg ctggaccggg acggcgacgg ctccacggcc    720
gacgccgatt gcaacgactt cgcgcccacc atccatccgg gcgccgccga agcgacgctg    780
gacggcgtgg attccaactg cgacgggcgc gactccggcg tggcggaagt cgtcgagacc    840
ttcaagaatc cgggcaccta ctccagcccg gtcatcaact tcaagatcgc ttcgccgccg    900
gggccgggaa cgcccatcta cgggccgccg cgtgatttct ccggttacaa caagagctac    960
tcgctggcga tcggcaagac ctcgtactac gatccgacca ccggcaccaa gtggaacgac   1020
gacaccatca cgccggtcag tgatggtcag gacatctggc gcggctggac ccataccggc   1080
aagtggtcgt tcttcaacgg caaggccggc gacaagatca ccctcagcgt acagcgtgat   1140
gcgcaggaag ccagcctgaa aggcgcccat ccgggcttca tcctgttctg gcggcccgag   1200
ggcggtccgc tgttctgggc cggcacccag gatctcgacg agggccagac cgcgctgccc   1260
gccgactccg acaccgttat cggccacgtg atcgttcagc acgccgactg gaccctgcag   1320
ggcttgccgc ccaaggccga ccataccgca cccgcgggcg tggataccga gctctatccc   1380
atgaagccgg acagctacac catgtactac gtcgactccg gctacgatgc cgacaagtac   1440
gtggcatcga agaagctcat catgcacccc acgcgttca agggctggc cctgaacgac      1500 ggcaccgccg gggcgttcac caagtccatc accctgccga agacgggcta ttacatgctg    1560
tacgtcgcca acgtcctgga agtggacgac tggagcgtcg acgcggacgg caagctcacc    1620
accaccggcg aagtctggga agtgccggcc aagggctgct gggtcaacat cacgatctcc    1680
aagcctacat tcgctccaat cctaaccctg gaccactct acaacgactc ccttgcaccc     1740
aacgatttca atcaatact tcttggctct acccagcttg acatcgcccc tgacggagcc     1800
gtctattcat tagatcggcc gctgtccatt gactacagtc tgggcactgg tgatgtcgac    1860
```

```
cgtgccgttt actggcatgt gaagaaagtt gctggcaatg cgggaacacc tgcggggtgg    1920
ttccactggg ggctatggga taatttcaac aaaacattca cacagggcgc tgcctactat    1980
tctgatgcgc agcctcgaca gatcttgctg ccagtgggca cgctcaacac ccgagctgac    2040
tcatgaccgg cttgatgtgc gtgatccttc ggagcggcca gtcgaccgtt ccgcggggaa    2100
aacttccgga gccaatcccc gtcctctgcg gcggggattt ttttattcgg cggaaccgag    2160
ttgggcgacg gcttttttcca gcttcttcaa ccggctccag atttcgtgca ggctcgaggg    2220
ggggcccggt acccagcttt tgttcccttt agtgagggtt aattgcgcgc ttggcgtaat    2280
catggtcata gctgtttcc                                                 2299
```

<210> SEQ ID NO 13
<211> LENGTH: 457
<212> TYPE: PRT
<213> ORGANISM: Methylococcus capsulatus

<400> SEQUENCE: 13

```
His Gly Leu Asp Thr Leu Asp Arg Asp Gly Asp Gly Ser Thr Ala Asp
1               5                  10                  15

Ala Asp Cys Asn Asp Phe Ala Pro Thr Ile His Pro Gly Ala Ala Glu
            20                  25                  30

Ala Thr Leu Asp Gly Val Asp Ser Asn Cys Asp Gly Arg Asp Ser Gly
        35                  40                  45

Val Ala Glu Val Val Glu Thr Phe Lys Asn Pro Gly Thr Tyr Ser Ser
    50                  55                  60

Pro Val Ile Asn Phe Lys Ile Ala Ser Pro Pro Gly Pro Gly Thr Pro
65                  70                  75                  80

Ile Tyr Gly Pro Pro Arg Asp Phe Ser Gly Tyr Asn Lys Ser Tyr Ser
                85                  90                  95

Leu Ala Ile Gly Lys Thr Ser Tyr Tyr Asp Pro Thr Thr Gly Thr Lys
            100                 105                 110

Trp Asn Asp Asp Thr Ile Thr Pro Val Ser Asp Gly Gln Asp Ile Trp
        115                 120                 125

Arg Gly Trp Thr His Thr Gly Lys Trp Ser Phe Phe Asn Gly Lys Ala
    130                 135                 140

Gly Asp Lys Ile Thr Leu Ser Val Gln Arg Asp Ala Gln Glu Ala Ser
145                 150                 155                 160

Leu Lys Gly Ala His Pro Gly Phe Ile Leu Phe Trp Arg Pro Glu Gly
                165                 170                 175

Gly Pro Leu Phe Trp Ala Gly Thr Gln Asp Leu Asp Glu Gly Gln Thr
            180                 185                 190

Ala Leu Pro Ala Asp Ser Asp Thr Val Ile Gly His Val Ile Val Gln
        195                 200                 205

His Ala Asp Trp Thr Leu Gln Gly Leu Pro Pro Lys Ala Asp His Thr
    210                 215                 220

Ala Pro Ala Gly Val Asp Thr Glu Leu Tyr Pro Met Lys Pro Asp Ser
225                 230                 235                 240

Tyr Thr Met Tyr Tyr Val Asp Ser Gly Tyr Asp Ala Asp Lys Tyr Val
                245                 250                 255

Ala Ser Lys Lys Leu Ile Met His Pro Thr Ala Phe Lys Gly Leu Ala
            260                 265                 270

Leu Asn Asp Gly Thr Ala Gly Ala Phe Thr Lys Ser Ile Thr Leu Pro
        275                 280                 285

Lys Thr Gly Tyr Tyr Met Leu Tyr Val Ala Asn Val Leu Glu Val Asp
```

```
                290                 295                 300
Asp Trp Ser Val Asp Ala Asp Gly Lys Leu Thr Thr Gly Glu Val
305                 310                 315                 320

Trp Glu Val Pro Ala Lys Gly Cys Trp Val Asn Ile Thr Ile Ser Lys
                325                 330                 335

Pro Phe Ala Pro Ile Leu Thr Leu Gly Pro Leu Tyr Asn Asp Ser Leu
                340                 345                 350

Ala Pro Asn Asp Phe Lys Ser Ile Leu Leu Gly Ser Thr Gln Leu Asp
                355                 360                 365

Ile Ala Pro Asp Gly Ala Val Tyr Ser Leu Asp Arg Pro Leu Ser Ile
                370                 375                 380

Asp Tyr Ser Leu Gly Thr Gly Asp Val Asp Arg Ala Val Tyr Trp His
385                 390                 395                 400

Val Lys Lys Val Ala Gly Asn Ala Gly Thr Pro Ala Gly Trp Phe His
                405                 410                 415

Trp Gly Leu Trp Asp Asn Phe Asn Lys Thr Phe Thr Gln Gly Ala Ala
                420                 425                 430

Tyr Tyr Ser Asp Ala Gln Pro Arg Gln Ile Leu Leu Pro Val Gly Thr
                435                 440                 445

Leu Phe Thr Arg Ala Asp Ser Gly Asn
                450                 455

<210> SEQ ID NO 14
<211> LENGTH: 2010
<212> TYPE: DNA
<213> ORGANISM: Methylococcus capsulatus

<400> SEQUENCE: 14
caaaatatta acgcttacaa tttccattcg ccattcaggc tgcgcaactg ttgggaaggg      60
cgatcggtgc gggcctcttc gctattacgc cagctggcga aaggggatg tgctgcaagg     120 cgattaagtt gggtaacgcc agggttttcc cagtcacgac gttgtaaaac gacggccagt     180
gagcgcgcgt aatacgactc actatagggc gaattggagc tcttaattaa tttccgcgca     240
gcccgattct ttcatggatc acgattccat gaatgcggc gaaatgtctc agggtccggt      300
cttgaatgaa gagttatggc ggcccagtac gtcaccgtta tgtccgatgg ctgtatcaaa     360
caaagacacg tgtagtgata tcggacaact cgtccatccc gtcgggagc attcggataa      420 tcgtgtcatc gttccaaaat attgatatat cggtatacgt atccgaagaa taaagttggc     480
acgatccctg taactaggtt gtcacgacct cgtcggaggt gtatgtccg gtgttccgtg      540 acgtcatcgg gcattcatca ttcatagaat gtgttacgga ggaaacaaca tatgagagac     600
accatgaacg aaaagcattg ctactcctta ctggccgccg gcctcatcgc cgccgtgccg     660
caactcgcag ccgcccatgg cctggacacg ctggaccggg acggcgacgg ctccacggcc     720
gacgccgatt gcaacgactt cgcgcccacc atccatccgg cgccgccga agcgacgctg     780 gacggcgtgg attccaactg cgacgggcgc gactccggcg tggcggaagt cgtcgagacc     840
ttcaagaatc cgggcaccta ctccagcccg gtcatcaact tcaagatcgc ttcgccgccg     900
gggccgggaa cgcccatcta cgggccgccg cgtgatttct ccggttacaa caagagctac     960
tcgctggcga tcggcaagac ctcgtactac gatccgacca ccggcaccaa gtggaacgac    1020
gacaccatca cgccggtcag tgatggtcag acatctggc gcggctggac ccataccggc    1080
aagtggtcgt tcttcaacgg caaggccgg acaagatca ccctcagcgt acagcgtgat    1140
gcgcaggaag ccagcctgaa aggcgcccat ccgggcttca tcctgttctg gcggcccgag    1200
```

-continued

```
ggcggtccgc tgttctgggc cggcacccag gatctcgacg agggccagac cgcgctgccc      1260
gccgactccg acaccgttat cggccacgtg atcgttcagc acgccgactg gaccctgcag      1320
ggcttgccgc ccaaggccga ccataccgca cccgcgggcg tggctagctc attagatcgg      1380
ccgctgtcca ttgactacag tctgggcact ggtgatgtcg accgtgccgc tagcgagctc      1440
tatcccatga agccggacag ctacaccatg tactacgtcg actccggcta cgatgccgac      1500
aagtacgtgg catcgaagaa gctcatcatg caccccacgg cgttcaaagg ctggccctg       1560 aacgacggca ccgccggggc gttcaccaag tccatcaccc tgccgaagac gggctattac      1620
atgctgtacg tcgccaacgt cctggaagtg acgactgga gcgtcgacgc ggacggcaag       1680
ctcaccacca ccggcgaagt ctgggaagtg ccggccaagg gctgctgggt caacatcacg      1740
atctccaagc cgtaaatccg gcttgatgtg cgtgatcctt cggagcggcc agtcgaccgt      1800
tccgcgggga aaacttccgg agccaatccc cgtcctctgc ggcggggatt tttttattcg      1860
gcggaaccga gttgggcgac ggcttttttcc agcttcttca accggctcca gatttcgtgc      1920
aggctcgagg gggggcccgg tacccagctt ttgttcccctt tagtgagggt taattgcgcg      1980
cttggcgtaa tcatggtcat agctgtttcc                                       2010
```

<210> SEQ ID NO 15
<211> LENGTH: 359
<212> TYPE: PRT
<213> ORGANISM: Methylococcus capsulatus

<400> SEQUENCE: 15

```
His Gly Leu Asp Thr Leu Asp Arg Asp Gly Asp Gly Ser Thr Ala Asp
1               5                   10                  15

Ala Asp Cys Asn Asp Phe Ala Pro Thr Ile His Pro Gly Ala Ala Glu
            20                  25                  30

Ala Thr Leu Asp Gly Val Asp Ser Asn Cys Asp Gly Arg Asp Ser Gly
        35                  40                  45

Val Ala Glu Val Val Glu Thr Phe Lys Asn Pro Gly Thr Tyr Ser Ser
    50                  55                  60

Pro Val Ile Asn Phe Lys Ile Ala Ser Pro Pro Gly Pro Gly Thr Pro
65                  70                  75                  80

Ile Tyr Gly Pro Pro Arg Asp Phe Ser Gly Tyr Asn Lys Ser Tyr Ser
                85                  90                  95

Leu Ala Ile Gly Lys Thr Ser Tyr Tyr Asp Pro Thr Thr Gly Thr Lys
            100                 105                 110

Trp Asn Asp Asp Thr Ile Thr Pro Val Ser Asp Gly Gln Asp Ile Trp
        115                 120                 125

Arg Gly Trp Thr His Thr Gly Lys Trp Ser Phe Phe Asn Gly Lys Ala
    130                 135                 140

Gly Asp Lys Ile Thr Leu Ser Val Gln Arg Asp Ala Gln Glu Ala Ser
145                 150                 155                 160

Leu Lys Gly Ala His Pro Gly Phe Ile Leu Phe Trp Arg Pro Glu Gly
                165                 170                 175

Gly Pro Leu Phe Trp Ala Gly Thr Gln Asp Leu Asp Glu Gly Gln Thr
            180                 185                 190

Ala Leu Pro Ala Asp Ser Asp Thr Val Ile Gly His Val Ile Val Gln
        195                 200                 205

His Ala Asp Trp Thr Leu Gln Gly Leu Pro Pro Lys Ala Asp His Thr
    210                 215                 220

Ala Pro Ala Gly Val Ala Ser Ser Leu Asp Arg Pro Leu Ser Ile Asp
225                 230                 235                 240
```

Tyr Ser Leu Gly Thr Gly Asp Val Asp Arg Ala Ala Ser Glu Leu Tyr
            245                 250                 255

Pro Met Lys Pro Asp Ser Tyr Thr Met Tyr Tyr Val Asp Ser Gly Tyr
        260                 265                 270

Asp Ala Asp Lys Tyr Val Ala Ser Lys Lys Leu Ile Met His Pro Thr
        275                 280                 285

Ala Phe Lys Gly Leu Ala Leu Asn Asp Gly Thr Ala Gly Ala Phe Thr
    290                 295                 300

Lys Ser Ile Thr Leu Pro Lys Thr Gly Tyr Tyr Met Leu Tyr Val Ala
305                 310                 315                 320

Asn Val Leu Glu Val Asp Asp Trp Ser Val Asp Ala Asp Gly Lys Leu
                325                 330                 335

Thr Thr Thr Gly Glu Val Trp Glu Val Pro Ala Lys Gly Cys Trp Val
            340                 345                 350

Asn Ile Thr Ile Ser Lys Pro
        355

<210> SEQ ID NO 16
<211> LENGTH: 1954
<212> TYPE: DNA
<213> ORGANISM: Methylococcus capsulatus

<400> SEQUENCE: 16
caaaatatta acgcttacaa tttccattcg ccattcaggc tgcgcaactg ttgggaaggg      60
cgatcggtgc gggcctcttc gctattacgc cagctggcga aagggggatg tgctgcaagg     120
cgattaagtt gggtaacgcc agggttttcc cagtcacgac gttgtaaaac gacggccagt     180
gagcgcgcgt aatacgactc actataggcc gaattgaggc tcttaattaa tttccgcgca     240
gcccgattct ttcatggatc acgattccat gaatgcggc gaaatgtctc agggtccggt      300
cttgaatgaa gagttatggc ggcccagtac gtcaccgtta tgtccgatgg ctgtatcaaa     360
caaagacacg tgtagtgata tcggacaact cgtccatccc cgtcgggagc attcggataa     420
tcgtgtcatc gttccaaaat attgatatat cggtatacgt atccgaagaa taaagttggc     480
acgatccctg taactaggtt gtcacgacct cgtcggaggt tgtatgtccg gtgttccgtg     540
acgtcatcgg gcattcatca ttcatagaat gtgttacgga ggaaacaaca tatgagagac     600
accatgaacg aaaagcattg ctactcctta ctggccgccg gcctcatcgc cgccgtgccg     660
caactcgcag ccgcccatgg cctggacacg ctggaccggg acggcgacgg ctccacggcc     720
gacgccgatt gcaacgactt cgcgcccacc atccatccgg gcgccgccga agcgacgctg     780
gacggcgtgg attccaactg cgacgggcgc gactccggcg tggcggaagt cgtcgagacc     840
ttcaagaatc cgggcaccta ctccagcccg gtcatcaact tcaagatcgc ttcgccgccg     900
gggccgggaa cgcccatcta cgggccgccg cgtgatttct ccggttacaa caagagctac     960
tcgctggcga tcggcaagac ctcgtactac gatccgacca ccggcaccaa gtggaacgac    1020
gacaccatca cgccggtcag tgatggtcag gacatctggc gcggctggac ccataccggc    1080
aagtggtcgt tcttcaacgg caaggccggc gacaagatca cctcagcgt acagcgtgat    1140
gcgcaggaag ccagcctgaa aggcgcccat ccgggcttca tcctgttctg gcggcccgag    1200
ggcggtccgc tgttctgggc cggcacccag gatctcgacg agggccagac cgcgctgccc    1260
gccgactccg acaccgttat cggccacgtg atcgttcagc acgccgactg gaccctgcag    1320
ggcttgccgc caaggccga ccataccgca cccgcgggcg tggataccga gctctatccc    1380
atgaagccgg acagctacac catgtactac gtcgactccg gctacgatgc cgacaagtac    1440

```
gtggcatcga agaagctcat catgcacccc acggcgttca aagggctggc cctgaacgac    1500
ggcaccgccg gggcgttcac caagtccatc accctgccga agacgggcta ttacatgctg    1560
tacgtcgcca acgtcctgga agtggacgac tggagcgtcg acgcggacgg caagctcacc    1620
accaccggcg aagtctggga agtgccggcc aagggctgct gggtcaacat cacgatctcc    1680
aagcctcatg accggcttga tgtgcgtgat ccttcggagc ggccagtcga ccgttccgcg    1740
gggaaaactt ccggagccaa tccccgtcct ctgcggcggg attttttta ttcggcggaa    1800 ccgagttggg cgacggcttt ttccagcttc ttcaaccggc tccagatttc gtgcaggctc    1860
gagggggggc ccggtaccca gcttttgttc cctttagtga gggttaattg cgcgcttggc    1920
gtaatcatgg tcatagctgt ttcctgtgtg aaat                                1954

<210> SEQ ID NO 17
<211> LENGTH: 1944
<212> TYPE: DNA
<213> ORGANISM: Methylococcus capsulatus

<400> SEQUENCE: 17
caaaatatta acgcttacaa tttccattcg ccattcaggc tgcgcaactg ttgggaaggg      60
cgatcggtgc gggcctcttc gctattacgc cagctggcga aaggggatg tgctgcaagg     120 cgattaagtt gggtaacgcc agggttttcc cagtcacgac gttgtaaaac gacgccagt     180 gagcgcgcgt aatacgactc actataggc gaattggagc tcttaattaa tttccgcgca     240
gcccgattct ttcatggatc acgattccat gaatgcggc gaaatgtctc agggtccggt     300
cttgaatgaa gagttatggc ggcccagtac gtcaccgtta tgtccgatgg ctgtatcaaa     360
caaagacacg tgtagtgata tcggacaact cgtccatccc gtcgggagc attcggataa     420 tcgtgtcatc gttccaaaat attgatatat cggtatacgt atccgaagaa taaagttggc     480
acgatccctg taactaggtt gtcacgacct cgtcggaggt tgtatgtccg gtgttccgtg     540
acgtcatcgg gcattcatca ttcatagaat gtgttacgga ggaaacaaca tatgagagac     600
accatgaacg aaaagcattg ctactcctta ctggccgccg gcctcatcgc cgccgtgccg     660
caactcgcag ccgcccatgg cctggacacg ctggaccggg acggcgacgg ctccacggcc     720
gacgccgatt gcaacgactt cgcgcccacc atccatccgg gcgccgccga agcgacgctg     780
gacggcgtgg attccaactg cgacgggcgc gactccggcg tggcggaagt cgtcgagacc     840
ttcaagaatc cggcaccta ctccagcccg gtcatcaact tcaagatcgc ttcgccgccg     900
gggccgggaa cgcccatcta cgggccgccg cgtgatttct ccggttacaa caagagctac     960
tcgctggcga tcggcaagac ctcgtactac gatccgacca ccggcaccaa gtggaacgac    1020
gacaccatca cgccggtcag tgatggtcag gacatctggc gcggctggac ccataccggc    1080
aagtggtcgt tcttcaacgg caaggccggc gacaagatca ccctcagcgt acagcgtgat    1140
gcgcaggaag ccagcctgaa aggcgcccat ccgggcttca tcctgttctg gcggcccgag    1200
ggcggtccgc tgttctgggc cggcacccag gatctcgacg agggccagac cgcgctgccc    1260
gccgactccg acaccgttat cggccacgtg atcgttcagc acgccgactg gaccctgcag    1320
ggcttgccgc ccaaggccga ccataccgca cccgcgggcg tggctagcga gctctatccc    1380
atgaagccgg acagctacac catgtactac gtcgactccg gctacgatgc cgacaagtac    1440
gtggcatcga agaagctcat catgcacccc acggcgttca aagggctggc cctgaacgac    1500
ggcaccgccg gggcgttcac caagtccatc accctgccga agacgggcta ttacatgctg    1560
tacgtcgcca acgtcctgga agtggacgac tggagcgtcg acgcggacgg caagctcacc    1620
```

| | |
|---|---|
| accaccggcg aagtctggga agtgccggcc aagggctgct gggtcaacat cacgatctcc | 1680 |
| aagccgtaaa tccggcttga tgtgcgtgat ccttcggagc ggccagtcga ccgttccgcg | 1740 |
| gggaaaactt ccggagccaa tccccgtcct ctgcggcggg gattttttta ttcggcggaa | 1800 |
| ccgagttggg cgacggcttt ttccagcttc ttcaaccggc tccagatttc gtgcaggctc | 1860 |
| gagggggggc ccggtaccca gcttttgttc cctttagtga gggttaattg cgcgcttggc | 1920 |
| gtaatcatgg tcatagctgt ttcc | 1944 |

<210> SEQ ID NO 18
<211> LENGTH: 1000
<212> TYPE: DNA
<213> ORGANISM: Methylococcus capsulatus

<400> SEQUENCE: 18

| | |
|---|---|
| taagaaattg gctaaaccag cgaccacaaa ggccgttaat ccccagcccc gtcgacgcaa | 60 |
| caacaaccgt cggcgtggca tgagagcgga tgcacccttta gctaaggcct cgactatcac | 120 |
| gggatttgga cgtgggacca atgacgtcca tctcacgggt atgtcgagaa tcgcccaagc | 180 |
| ggttatccca gctggcaccg gcacggacgg atacatcgtg gttgacgaaa ccatcgtccc | 240 |
| cgagctcttg ccaagactgg gatttgctgc tagaatcttc cagcgatacg ctgttgagac | 300 |
| actggagttc gaaattcagc caatgtgccc cgcaaacacg ggcggtggtt acgtggctgg | 360 |
| cttcctgcct gatccaactg acagcgacca ccttcgac gcaattcaag cgactcgcgg | 420 |
| tgcggtcgtt gccaaatggt gggaaagcag aacaatccga ccccagcatg cccgcgcact | 480 |
| cctctggacc tcggtcggga aggagcagcg tttgacatcc ccgggccggt tggtactcct | 540 |
| gtgtgccggc aacaacactg acgtcgtcaa cgtgtcagtg ctgtgtcgct ggagtgtacg | 600 |
| tctcagtgtt ccatctctcg agacacctga agatacattc gctccaatcc taaccctggg | 660 |
| accactctac aacgactccc ttgcacccaa cgatttcaaa tcaatacttc ttggctctac | 720 |
| ccagcttgac atcgcccctg acggagccgt ctattcatta gatcggccgc tgtccattga | 780 |
| ctacagtctg ggcactggtg atgtcgaccg tgccgtttac tggcatgtga agaaagttgc | 840 |
| tggcaatgcg ggaacacctg cggggtggtt ccactggggg ctatgggata atttcaacaa | 900 |
| aacattcaca cagggcgctg cctactattc tgatgcgcag cctcgacaga tcttgctgcc | 960 |
| agtgggcacg ctcttcaccc gagctgactc gggaaactaa | 1000 |

<210> SEQ ID NO 19
<211> LENGTH: 6700
<212> TYPE: DNA
<213> ORGANISM: Methylococcus capsulatus

<400> SEQUENCE: 19

| | |
|---|---|
| ctcgggccgt ctcttgggct tgatcggcct tcttgcgcat tcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgcccgt | 480 |
| acttgtccgc cagccacttg tgcgccttct cgaagaacgc cgcctgctgt tcttggctgg | 540 |

```
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg acaagctga    1080 tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380 tgcccccga gcctcacggc ggcgagtgcg ggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaaatcaa caacttaaaa aaggggggta   1620
cgcaacagct cattgcggca ccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagcggg ccacctcga   2580 cctgaatgga agccggcggc acctcgctaa cggattcacc gtttttatca ggctctggga   2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaacca   2880
ggcgtttaag ggcaccaata actgccttaa aaaaattacg ccccgccctg ccactcatcg   2940
```

```
cagtacggcc tattggttaa aaaatgagct gatttaacaa aaatttaacg cgaattttaa    3000
caaaatatta acgcttacaa tttccattcg ccattcaggc tgcgcaactg ttgggaaggg    3060
cgatcggtgc gggcctcttc gctattacgc cagctggcga aaggggatg tgctgcaagg    3120 cgattaagtt gggtaacgcc agggttttcc cagtcacgac gttgtaaaac gacggccagt    3180
gagcgcgcgt aatacgactc actatagggc gaattggagc tcttaattaa tttccgcgca    3240
gcccgattct ttcatggatc acgattccat tgaatgcggc gaaatgtctc agggtccggt    3300
cttgaatgaa gagttatggc ggcccagtac gtcaccgtta tgtccgatgg ctgtatcaaa    3360
caaagacacg tgtagtgata tcggacaact cgtccatccc cgtcgggagc attcggataa    3420
tcgtgtcatc gttccaaaat attgatatat cggtatacgt atccgaagaa taaagttggc    3480
acgatccctg taactaggtt gtcacgacct cgtcggaggt tgtatgtccg gtgttccgtg    3540
acgtcatcgg gcattcatca ttcatagaat gtgttacgga ggaaacaaca tatgagagac    3600
accatgaacg aaaagcattg ctactcctta ctggccgccg gcctcatcgc cgccgtgccg    3660
caactcgcag ccgcccatgg cctggacacg ctggaccggg acggcgacgg ctccacggcc    3720
gacgccgatt gcaacgactt cgcgcccacc atccatccgg gcgccgccga agcgacgctg    3780
gacggcgtgg attccaactg cgacgggcgc gactccggcg tggcggaagt cgtcgagacc    3840
ttcaagaatc cgggcaccta ctccagcccg gtcatcaact tcaagatcgc ttcgccgccg    3900
gggccgggaa cgcccatcta cgggccgccg cgtgatttct ccggttacaa caagagctac    3960
tcgctggcga tcggcaagac ctcgtactac gatccgacca ccggcaccaa gtggaacgac    4020
gacaccatca cgccggtcag tgatggtcag gacatctggc gcggctggac ccataccggc    4080
aagtggtcgt tcttcaacgg caaggccggc gacaagatca ccctcagcgt acagcgtgat    4140
gcgcaggaag ccagcctgaa aggcgcccat ccgggcttca tcctgttctg gcggcccgag    4200
ggcggtccgc tgttctgggc cggcacccag gatctcgacg agggccagac cgcgctgccc    4260
gccgactccg acaccgttat cggccacgtg atcgttcagc acgccgactg gaccctgcag    4320
ggcttgccgc caaggccga ccataccgca cccgcgggcg tggataccga gctctatccc    4380
atgaagccgg acagctacac catgtactac gtcgactccg gctacgatgc cgacaagtac    4440
gtggcatcga agaagctcat catgcacccc acggcgttca aagggctggc cctgaacgac    4500
ggcaccgccg gggcgttcac caagtccatc accctgccga agacgggcta ttacatgctg    4560
tacgtcgcca acgtcctgga agtggacgac tggagcgtcg acgcggacgg caagctcacc    4620
accaccggcg aagtctggga agtgccggcc aagggctgct gggtcaacat cacgatctcc    4680
aagccgtaaa tccggcttga tgtgcgtgat ccttcggagc ggccagtcga ccgttccgcg    4740
gggaaaactt ccggagccaa tccccgtcct ctgcggcggg gatttttta ttcggcggaa    4800 ccgagttggg cgacggcttt ttccagcttc ttcaaccggc tccagatttc gtgcaggctc    4860 gaggggggc ccggtaccca gcttttgttc cctttagtga gggttaattg cgcgcttggc    4920
gtaatcatgg tcatagctgt ttcctgtgtg aaattgttat ccgctcacaa ttccacacaa    4980
catacgagcc ggaagcataa agtgtaaagc ctggggtgcc taatgagtga gctaactcac    5040
attaattgcg ttgcgctcac tgcccgcttt ccagtcggga aacctgtcgt gccagctgca    5100
ttaatgaatc ggccaacgcg cggggagagg cggtttgcgt attgggcgca tgcataaaaa    5160
ctgttgtaat tcattaagca ttctgccgac atggaagcca tcacaaacgg catgatgaac    5220
ctgaatcgcc agcggcatca gcaccttgtc gccttgcgta taatatttgc ccttgggggt    5280
gggcgaagaa ctccagcatg agatccccgc gctggaggat catccagccg gcgtcccgga    5340
```

```
aaacgattcc gaagcccaac ctttcataga aggcggcggt ggaatcgaaa tctcgtgatg    5400
gcaggttggg cgtcgcttgg tcggtcattt cgaacccag agtcccgctc agaagaactc     5460
gtcaagaagg cgatagaagg cgatgcgctg cgaatcggga gcggcgatac cgtaaagcac    5520
gaggaagcgg tcagcccatt cgccgccaag ctcttcagca atatcacggg tagccaacgc    5580
tatgtcctga tagcggtccg ccacacccag ccggccacag tcgatgaatc cagaaaagcg    5640
gccattttcc accatgatat tcggcaagca ggcatcgcca tgggtcacga cgagatcctc    5700
gccgtcgggc atgcgcgcct tgagcctggc gaacagttcg gctggcgcga gcccctgatg    5760
ctcttcgtcc agatcatcct gatcgacaag accggcttcc atccgagtac gtgctcgctc    5820
gatgcgatgt ttcgcttggt ggtcgaatgg gcaggtagcc ggatcaagcg tatgcagccg    5880
ccgcattgca tcagccatga tggatacttt ctcggcagga gcaaggtgag atgacaggag    5940
atcctgcccc ggcacttcgc ccaatagcag ccagtcccctt cccgcttcag tgacaacgtc    6000
gagcacagct gcgcaaggaa cgcccgtcgt ggccagccac gatagccgcg ctgcctcgtc    6060
ctgcagttca ttcagggcac cggacaggtc ggtcttgaca aaagaaccg ggcgcccctg    6120 cgctgacagc cggaacacgg cggcatcaga gcagccgatt gtctgttgtg cccagtcata    6180
gccgaatagc ctctccaccc aagcggccgg agaacctgcg tgcaatccat cttgttcaat    6240
catgcgaaac gatcctcatc ctgtctcttg atcagatctt gatccctgc gccatcagat     6300 ccttggcggc aagaaagcca tccagtttac tttgcagggc ttcccaacct taccagaggg    6360
cgccccagct ggcaattccg gttcgcttgc tgtccataaa accgcccagt ctagctatcg    6420
ccatgtaagc ccactgcaag ctacctgctt tctctttgcg cttgcgtttt cccttgtcca    6480
gatagcccag tagctgacat tcatcccagg tggcactttt cggggaaatg tgcgcgcccg    6540
cgttcctgct ggcgctgggc ctgtttctgg cgctggactt cccgctgttc cgtcagcagc    6600
ttttcgccca cggccttgat gatcgcgcg gccttggcct gcatatcccg attcaacggc    6660
cccagggcgt ccagaacggg cttcaggcgc tcccgaaggt                           6700
```

<210> SEQ ID NO 20
<211> LENGTH: 33
<212> TYPE: DNA
<213> ORGANISM: Methylococcus capsulatus

<400> SEQUENCE: 20
gtggagccgt tgccgttccg gttcagcgtg tcc                                  33

<210> SEQ ID NO 21
<211> LENGTH: 21
<212> TYPE: DNA
<213> ORGANISM: Methylococcus capsulatus

<400> SEQUENCE: 21
tggcggtgat ctcgagcctg c                                               21

<210> SEQ ID NO 22
<211> LENGTH: 20
<212> TYPE: DNA
<213> ORGANISM: Methylococcus capsulatus

<400> SEQUENCE: 22
agtgcctcca tgggcggctg                                                 20

<210> SEQ ID NO 23
<211> LENGTH: 23

```
<212> TYPE: DNA
<213> ORGANISM: Methylococcus capsulatus

<400> SEQUENCE: 23
cagcgaactc ccatggcctg gac                                          23

<210> SEQ ID NO 24
<211> LENGTH: 38
<212> TYPE: DNA
<213> ORGANISM: Methylococcus capsulatus

<400> SEQUENCE: 24
gcaaaccatg gtaagaaatt ggctaaacca gcgaccac                          38

<210> SEQ ID NO 25
<211> LENGTH: 30
<212> TYPE: DNA
<213> ORGANISM: Methylococcus capsulatus

<400> SEQUENCE: 25
ttagtccatg gagtcagctc gggtgttgag                                   30

<210> SEQ ID NO 26
<211> LENGTH: 27
<212> TYPE: DNA
<213> ORGANISM: Methylococcus capsulatus

<400> SEQUENCE: 26
gccatgggag tcagctcggg tgttgag                                      27

<210> SEQ ID NO 27
<211> LENGTH: 27
<212> TYPE: DNA
<213> ORGANISM: Methylococcus capsulatus

<400> SEQUENCE: 27
tcatgataca ttcgctccaa tcctaac                                      27

<210> SEQ ID NO 28
<211> LENGTH: 30
<212> TYPE: DNA
<213> ORGANISM: Methylococcus capsulatus

<400> SEQUENCE: 28
ttagtctcat gagtcagctc gggtgttgag                                   30

<210> SEQ ID NO 29
<211> LENGTH: 21
<212> TYPE: DNA
<213> ORGANISM: Methylococcus capsulatus

<400> SEQUENCE: 29
ctccaagcct acattcgctc c                                            21

<210> SEQ ID NO 30
<211> LENGTH: 66
<212> TYPE: DNA
<213> ORGANISM: Methylococcus capsulatus

<400> SEQUENCE: 30
ctagctcatt agatcggccg ctgtccattg actacagtct gggcactggt gatgtcgacc  60
gtgccg                                                             66
```

```
<210> SEQ ID NO 31
<211> LENGTH: 66
<212> TYPE: DNA
<213> ORGANISM: Methylococcus capsulatus

<400> SEQUENCE: 31
ctagcggcac ggtcgacatc accagtgccc agactgtagt caatggacag cggccgatct    60
aatgag                                                                66

<210> SEQ ID NO 32
<211> LENGTH: 22
<212> TYPE: DNA
<213> ORGANISM: Methylococcus capsulatus

<400> SEQUENCE: 32
gcgtggctag cacattcgct cc                                              22

<210> SEQ ID NO 33
<211> LENGTH: 22
<212> TYPE: DNA
<213> ORGANISM: Methylococcus capsulatus

<400> SEQUENCE: 33
ccgagctgac gctagcgagc tc                                              22
```

SYSTEMS FOR EXPRESSION OF HETEROLOGOUS PROTEINS IN M. CAPSULATUS

FIELD OF THE INVENTION

The present invention relates to the expression of heterologous proteins in the bacteria *M. capsulatus*. More specifically, the present invention relates to the exportation and display of polypeptides and proteins on the surface of said bacteria.

Thus, the present application relates to a recombinant vector, a bacterial host cell transformed with said vector, a method for producing a desired protein in a bacterial host cell, a protein capable of being exposed on the surface of a methanotrophic bacterium, and a fusion protein.

BACKGROUND OF THE INVENTION

The expression of polypeptides on the surface of bacteria and bacteriophages has been pursued for several years, in part because of interest in recombinant antibody production. Many other potential applications exist, including the production of genetically-engineered whole cell adsorbents, construction of "peptide libraries", cell bound enzymes, and use as live vaccines or immunogens to generate antibodies.

In bacteria, one approach to obtaining surface expressed foreign proteins has been the use of native membrane proteins as a carrier for a foreign protein. In general, most attempts to develop methods of anchoring proteins on a bacterial surface have focused on fusion of the desired recombinant polypeptide to a native protein that is normally exposed on the cell's exterior with the hope that the resulting hybrid will also be localized on the surface.

In a prior invention (Norwegian patent application no. 20033176) the present inventors also provided an expression system where a heterologous polypeptide (termed "desired" protein) was expressed in the bacteria *Methylococcus capsulatus*. The heterologous protein is preferably linked to an outer membrane protein in *M. capsulatus* termed MopE.

MopE has a 540 amino acid protein sequence, with a short (29 amino acids) N-terminal sequence dependent signal sequence, followed by a N-terminal domain (176 amino acids) and a C-terminal domain (335 amino acids). The N-terminal domain is not secreted, while the C-terminal domain is secreted and expressed on the cell surface. The MopE amino acid sequence is shown in the sequence listing, as SEQ. ID. NO. 1

The method of secretion is not known. MopE does not show high sequence similarity to other known secreted proteins. The secretion is host specific, although inserted in the IM and released to the periplasm, the MopE protein is not secreted by *E. coli* hosts, only by *M. capsulatus*. MopE has been proposed to be secreted either by the Type 2 Secretion system (T2S) or the Type 5 Secretion system (T5S) based upon its primary sequence (Fjellbirkeland et al., 2001). Proteins secreted by the T2S or T5S systems can be translocated across the IM either by the Tat or the Sec machinery, which are shown in FIG. 1.

Secretion of T2S substrates is very host specific. Secretion by the T2S system (FIG. 1) is a two-step process in which the secreted protein initially is exported across the IM by the Sec or Tat export systems. The periplasmatic intermediate is subsequently translocated across the OM by the T2S secretion through the channel formed by the secretin that is large enough to translocate folded or close to folded substrates. T2S is energized by ATP, and although not required for secretion, the proton motive force increases the rate of secretion.

Substrates of the T2S system share no obvious similarities in primary sequence. Although no recognition signal that confine proteins to secretion by the T2S pathway has been identified, a potential common feature for T2S substrates is a medium to high content of β-sheet (de Vries et al., 1990 and Sandkvist, 2001). β-strands were predicted in the N-terminal domain of MopE by the computer program PRED-TMBB (http://bioinfromatics.biol.uoa.gr/PRED-TMBB), and this program also predicted an N-terminal β-barrel in MopE. The predicted β-strands may form the tertiary structures of β-sheets required for translocation by the T2S pathway. In addition to the prediction of such structures in N-terminal domain of Mop-E, MopE$^C$ is heat-modifiable while MopE* is not (Fjellbirkeland et al., 2001), indicating that the N-terminal domain of MopE indeed contains stabile β-structures, and thus is a candidate T2S substrate. Since a Sec-compatible signal sequence has been predicted in MopE it has been considered likely that the Sec machinery export MopE across the IM.

However, the presence of β-structures does not confine secreted proteins to the T2S route. Substrates of T5S, autotransporters, require a β-domain that forms a β-barrel that allows for translocation of the passenger domain across the OM. Since the N-terminal domain of MopE has the potential of containing β-structures, the domain could function as an autotransporter translocation unit in T5S. No autoproteolytic activity could be demonstrated for MopE using the substrate azocasein, however, such activity is not a widely distributed feature among T5S substrates, and thus not required. And while autotransporters inherently contain all information and accessory factors necessary for translocation to the OM, release of the protein to the extracellular space most often require cleavage by an external protease. Thus secretion by T5S is somewhat dependent on the host cell, and the host specificity observed for the secretion of MopE does not exclude secretion by the T5S route.

Thus, it was thought that the most likely mechanism for translocation of MopE was either by the T2S or T5S routes, by the Sec or Tat transport systems. This translocation would then require the β-structures found in the N-terminal domain of MopE. Thus it was expected that the removal of the N-terminal domain of MopE would abolish the ability of the truncated protein, here termed MopE$^{H}$*, to translocate. The MopE$^{H}$* amino acid sequence is shown in the sequence listing, as SEQ. ID. NO. 2.

SUMMARY OF THE INVENTION

The inventors constructed a mutated MopE protein, MopE$^{H}$*, that consisted of the secreted domain of MopE alone, and did not contain the N-terminal MopE domain. (Please see FIG. 2 for a comparison of MopE and MopE$^{H}$*) Quite surprisingly, they found that MopE$^{H}$* fully retained its' ability to translocate in *M. capsulatus.*

Experiments were also performed to ascertain the usefulness of MopE$^{H}$* as part of a fusion protein capable of translocation, by expressing Atlantic halibut nodavirus capsid protein fused to the surface protein MopE. As shown below, these fusion proteins were indeed capable of translocation.

As stated, this translocation of MopE$^{H}$*, with or without a fused protein, is very surprising because it was thought that the N-terminal of MopE was required for translocation by the T2S or T5S routes. In addition, even though a protein in its entirety, here MopE, is known to be translocated, there is no reason to believe that only parts of the protein also may be able to do so.

The importance of this invention is fairly self evident. If one is to use MopE as a translocation system, there is an advantage to narrow it down to the smallest possible protein. There are always limits to how large of a protein (i.e. how long of a amino acid chain) may be transported. By removing a part of the native protein (here the N-terminal domain) one may, as shown, fuse a proportionally larger protein to the truncated MopE protein, and still have a reasonable expectation of successful translocation. In addition, the discovery that the N-terminal is not involved in translocation, changes the understanding of how MopE is translocated, and points research in new directions in trying to ascertain the mechanisms behind the translocation.

BRIEF DESCRIPTION OF THE DRAWINGS

The invention can be better understood with reference to the following figures.

Figure 1:
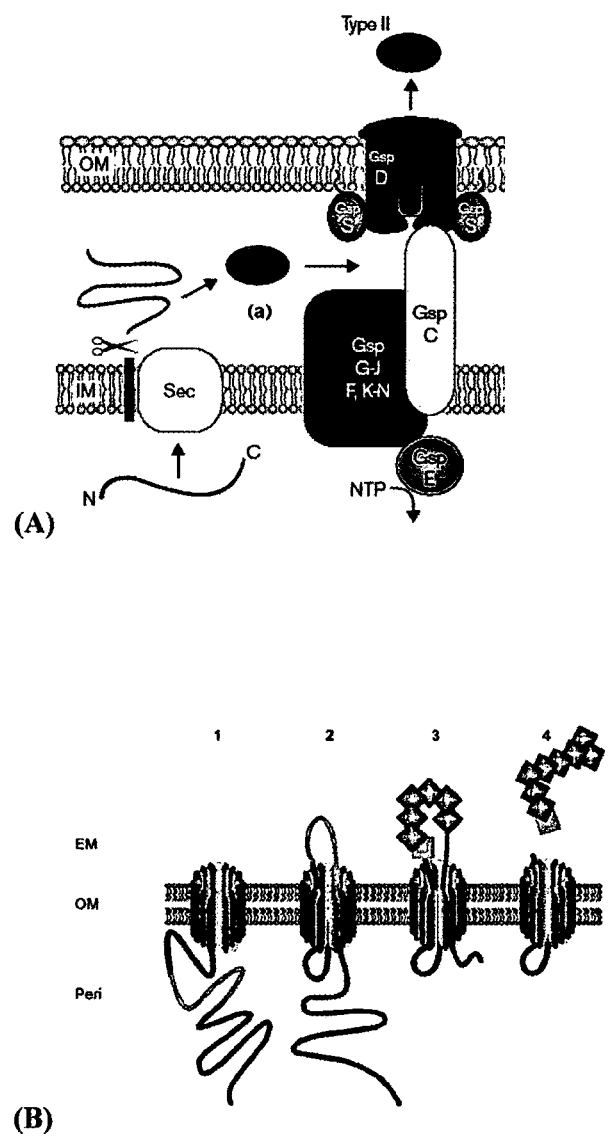
FIG. 1. Overview of secretion by the Type 2 and Type 5 secretion systems. (A) The T2S system secretion consists of 12-16 proteins depending of species. The majority of the T2S components are IM proteins, many with large periplasmatic domains. Two of these GspE and GspL interact with ATP and are involved in energizing of the secretion. In the OM 12-14 GspD and GspS units form a secretin. The secretin is a transmembrane complex with a channel 5-10 nm in diameter, thus large enough to translocate folded or close to folded polypeptides. (B) Proteins secreted by T5S are pre-pro-proteins consisting of three domains: an N-terminal signal sequence for export across the IM, an internal passenger/functional domain and a C-terminal β-domain. The Figures (A) and (B) are reproduced from (Voulhoux et al., 2001) and (Desvaux et al., 2004), respectively.

DETAILED DESCRIPTION OF THE INVENTION

Cultured *Methylococcus capsulatus* with pBBmopE$^{H}$* plasmid was deposited with DDZ access identification *Methylococcus capsulatus* McdeltamopEpBBmopEH=DSM 19108 on Mar. 1, 2007 with DSMZ-Deutsche Sammlung von Mikroorganismen and Zellkulturen GmbH (The German National Resource Centre for Biological Material), Inhoffenstr. 7 B, D-38124 Braunschweig, Germany.

A sequence listing was prepared using PatentIn3.4 for the amino acid sequences of MopE (SEQ. ID. NO. 1) and MopEH* (SEQ. ID. NO. 2), AHNVC-MopEH* fusion protein (SEQ. ID. NO. 11), MopEH*-AHNVCc fusion protein (SEQ. ID. NO. 13), MopEH*-AHNVC-20 aa fusion protein (SEQ. ID. NO. 15), and the DNA sequences of MopE (SEQ. ID. NO. 3), MopEH* (SEQ. ID. NO. 4), pET1 (SEQ. ID. NO. 5), pET2 (SEQ. ID. NO. 6), pCR2.1-TOPO1 (SEQ. ID. NO. 7), pCR2.1-TOPO2 (SEQ. ID. NO. 8), and pBBmopEH*

(SEQ. ID. NO. 9), AHNVC-MopEH* (SEQ. ID. NO. 10), MopEH*-AHNVC (SEQ. ID. NO. 12), MopEH*-AHNVC-20 aa (SEQ. ID. NO. 14), MopEH* with BspHI mutation in stop codon (SEQ. ID. NO. 16), MopEH* with NdeI mutation (SEQ. ID. NO. 17), Atlantic halibut Nodavirus capsid protein 2 (SEQ. ID. NO. 18) and pBBR1-mopEH*(SEQ. ID. NO. 19). The primers given in tables 4 and 6 are also given as PatentIn SEQ. ID. NOs. 22-23. MopEH ST25. txt PatentIn utskrift Thus, the recombinant vector according to the present invention comprise a first nucleotide sequence SEQ. ID. NO. 4, or sequences homologous thereto, capable of translocation through the outer membrane of *Methylococcus capsulatus*.

Also, the bacterial host cell according to the present invention is transformed with said recombinant vector.

And, the method for producing a desired protein in a bacterial host cell according to the present invention comprise transforming a bacterial host cell with a recombinant vector comprising a first nucleotide sequence SEQ. ID. NO. 4 or sequences homologous thereto, and said vector comprising a further nucleotide sequence encoding said protein, said further nucleotide sequence being operably linked in frame to said first nucleotide sequence, and culturing said transformed host cell in a suitable medium under conditions allowing expression of said protein.

And, the protein capable of being exposed on the surface of a methanotrophic bacterium according to the present invention is encoded for by SEQ. ID. NO. 2 or sequences homologous thereto.

And, the fusion protein according to the present invention comprise a protein or peptide sequence encoded for by a nucleotide sequence SEQ. ID. NO. 4 or sequences homologous thereto, and a desired protein or peptide, capable of being translocated.

The fusion protein according to the invention is preferably expressed from a chimeric DNA having a DNA segment encoding a leader amino acid sequence capable of mediating secretion of the fusion protein, a DNA segment encoding for subunits of the surface protein, and a DNA segment encoding the desired target protein. The DNA segments are positioned such that expression of the fusion protein results in display of the target protein on the surface of the cells. The fusion proteins are preferably anchored to the cell surface of the bacteria forming what is referred to as a "display bacteria."

The present invention thus provides for a system for the expression of heterologous proteins, where the heterologous proteins are expressed on the surface of the bacterial cells.

The chimeric DNA may be integrated into the bacterial cell chromosome or be carried by a vector, where said vector preferably dose not comprise the entire nucleotide sequense of MopE (SEQ. ID. NO. 3), but rather only the truncated sequence comprising MopE$^H$*(SEQ. ID. NO. 4). In certain preferred embodiments, expression of the fusion protein may be regulated by an inducible promoter. Bacteria displaying a particular protein may be selected, for example, using antibody affinity. The fusion protein can be detached from selected cells. If desired, the target protein may be separated from the surface protein and further purified. Target proteins useful in the present invention include peptides, proteins, e.g., hormones, enzymes, inhibitors, and receptors, antigens, antibodies including antibody fragments and single-chain antibodies.

The present invention thus provides a system for the expression of heterologous proteins in the membrane fraction, and preferable on the cell surface of the *M. capsulatus*.

The bacterium *M. capsulatus* is able to utilise methane as a single carbon and energy source. Bacteria capable of oxidising methane are collectively referred to as methanotrophs. They belong to different families and groups of the eubacteria but have in common the possession of the unusual enzyme methane mono oxygenase, which catalyses the oxidation of methane to methanol.

The bacterium has an obligate requirement for methane or methanol and an optimum growth temperature of 45° C. Methane is oxidized via methanol to formaldehyde which is either assimilated into cellular biomass or dissimilated to carbon dioxide to release cellular energy.

*M. capsulatus* has a gram-negative cell envelope. Much of the intracellular space is occupied by an extensive intracytoplasmic membrane system. The genome of *M. capsulatus* (Bath) has a molecular weight of $2.8 \times 10^9$ Da and a G+C content of 62.5%.

Commercial interests involving *M. capsulatus* and other methanotrophs could roughly be divided into two categories: Those taking advantage of the inexpensive growth requirements of the bacteria and those taking advantage of unique catalytic activities possessed by the bacteria.

The development of high-cell density fermentation technology for *M. capsulatus* has created the possibility of producing large quantities of specialised compounds like for instance amino acids, cofactors, vitamins, metabolic end products, and various high value proteins, at reasonable costs.

The present invention thus provides a system for the manufacturing of such product.

Other uses for the protein display methods of the present invention include, for example, epitope mapping, screening of antibody libraries and live bacterial vaccines.

The invention is especially suited for production of vaccines that can be administered orally for use in animals, fish and humans. The technique can also potentially be used for display of vaccines, especially for oral administration.

The invention relates to the use of the genes and the proteins encoded by them, as given in the accompanying sequences list, fragments thereof, or functionally equivalent substantially similar genes, for construction of fusion proteins carrying foreign peptide sequences for display in the *M. capsulatus*, and preferable on the surface of said bacterium. The term "homology" or "homologous", as used in the present application, does not necessary infer a common evolutionary ancestor/relationship, as homologous sequences may be artificially created. Rather, it is meant to encompass sequences that are similar and have a similar function, that is, sequences likely to be able to perform the same/similar function due to having a degree of sequence similarity (that may be defined as a percentage sequence similarity/identity).

*M. capsulatus* is a bacterium licensed for use in animal and fish feed. It has no virulent or pathogenic properties, and contains very low amounts of endotoxin (LPS). It is thus well suited as a carrier organism for recombinant oral vaccines, with a potential also for use in humans. Vaccines could be constructed by insertion of fragments of D15 genes from pathogens into the *M. capsulatus* D15 gene in order to display a fusion-protein containing parts of the two D15 antigens on the surface of *M. capsulatus*. The part of the D15 protein originating from the pathogen should trigger an immune response to the respective pathogenic bacterium. If replacement of *M. capsulatus*-specific D15 sequences with corresponding sequences from the pathogens is well tolerated by the host, larger regions of D15 could be replaced, and if possible, the entire D15 protein could be replaced by the corresponding protein from a pathogen.

Due to the sequence conservation of D15 among distantly related bacteria, exchange of parts of the gene (or the entire gene) without seriously affecting the survival and growth of

*M. capsulatus* is plausible. The specific function of the D15 antigen on the surface of the bacteria is not known, but it possibly plays a structural role and is most probably not involved in any important biochemical processes.

Successful display of the target protein on the cell surface can be detected using a number of methods, for example, if the target peptide can be specifically labeled by a procedure that does not operate through the membrane, its cell surface display can be readily demonstrated.

If the target polypeptide displays enzymatic activity, one may use such activity to demonstrate cell surface display. Antibodies against the target protein may also be used.

The chimeric DNA may be integrated into the host cell chromosome or be carried within a vector. Methods of integrating DNA into a host cell chromosome are well known in the art. The chimeric DNA may also be carried within a recombinant vector, e.g., a plasmid.

Plasmids useful as the vector backbone include plasmids containing replicon and control sequences which are derived from species compatible with the host cell. The vector may also contain an inducible promoter and marker gene, e.g., antibiotic resistance.

Introduction of the chimeric DNA to the host cell may be effected by any method known to those skilled in the art. For example, if a recombinant vector carries the DNA, the vector can be introduced, for example, by transformation, electroporation, or phage transfection.

The detection techniques noted above can be used initially to verify that the method of the present invention is working, i.e., that the fusion surface protein has been expressed and transported to the bacterial cell surface and is orientated so that the target protein is accessible i.e., displayed.

Cells that display the target may be separated from those that do not, using, for example, affinity separation techniques. Such techniques include affinity column chromatography, batch elution from affinity matrix material and fluorescent-activated cell sorting.

MopE is a major outer membrane protein of *M. capsulatus*. It contains surface-exposed regions but its exact folding and association with the cell surface is not known. Under copper limitations, the C-terminal part of the protein is secreted into the growth medium, but considerable amounts of the full-length protein remains associated with the cell surface. By using this protein as an anchor it is possible to mediate translocation of passenger proteins to the cell surface or to the extracellular environment.

Experimental Section

Bacterial Strains

*M. capsulatus*

TABLE 1

Strains of *M. capsulatus* used.

| Strain | Description and use | Reference |
| --- | --- | --- |
| *M. capsulatus* (Bath) wild type NCIMB 11132 | Used as control and reference. | Whittenbury et al., 1970 |
| *M. capsulatus* ΔmopE | Contains an inactivated mopE gene and is gentamycin resistant. Used as host for plasmids expressing mutated MopE protein and as mating-pair recipient in conjugation with *E. coli* S17-1 | Fjellbirkeland unpublished |

*E. coli*

TABLE 2

Stains of *E. coli* used.

| Strain | Description and use | Reference |
| --- | --- | --- |
| One Shot TOP10F' | Genotype: F' [lacI$^q$Tn10 (Tet$^R$)] mcrA ?(mrr- hsdRMS-mcrBC) Φ80lacZ?M15 ?lacX74 recA1araD139 ?(ara-leu)7697 galU galK rpsL (Str$^R$) endA1 nupG Used as intermediate host for constructed plasmids, and as host for TOPO TA cloning. | Invitrogen |
| S17-1 | Genotype: Tp$^R$ Sm$^R$ recA, thi, pro, hsdR-M + RP4: 2-Tc:Mu: Km Tn7 1 pir Has genomically inserted tra genes and were used as mating-pair donor in conjugation with *M. capsulatus* ΔmopE. | Simon et al., 1983 |
| DH5α | Genotype: supE44 DlacU169 (F80 lacZDM15) hsdR17 recA1 endA1 gyrA96 thi-1 relA1 Host for plasmids pAFpg10 and pJBrp2. | Invitrogen |

Plasmids

TABLE 3

List of plasmids used.

| Name | Description and use | Reference |
|---|---|---|
| pAFpg10 | Contained both mopE and $Amp^R$. Used as template for PCR amplification of the truncated mopE gene, $mopE^{H*}$, and for site-directed mutagenesis to create mopE genes mutated by substitution, the $mopE^{dn}$ genes. | Fjellbirkeland et al., 2001 |
| pJBrp2 | Contained $Km^R$, the copper-sensitive mmoX promoter and the sequence encoding the MopE signal sequence. Used for PCR amplification of the mmoX promoter and the sequence encoding the MopE signal sequence. | Haugland, unpublished |
| pCR ®2.1 | Used in subcloning of an amplification product containing mmoX promoter and the sequence encoding the MopE signal sequence or $mopE^{H*}$ by TA TOPO cloning. Linear and with 3'-T overhang. Contained lacZα, $Km^R$, $Amp^R$, F1 ori and pUCori. | INVITROGEN |
| pCR ®2.1 TOPO1 | Cloning intermediate based on pCR ®2.1 that contain the mmoX promoter linked to the sequence encoding the MopE signal sequence. Also contained $Km^R$, $Amp^R$ and LacZα disrupted by insertion of the DNA fragment. | This application |
| pCR ®2.1 TOPO2 | Cloning intermediate based on pCR ®2.1 that contain $mopE^{H*}$. Also contained $Km^R$, $Amp^R$ and LacZα disrupted by insertion of the $mopE^{H*}$ gene. | This application |
| pET11d | Intermediate vector used to connect the mmoX promoter, the sequence encoding the MopE signal sequence and the $mopE^{H*}$ gene. Also contained $Amp^R$, pBR322 ori, lacIq and lac operator. | Stratagene |
| pET1 | Cloning intermediate based on pET11d that contain the mmoX promoter linked to the sequence encoding the MopE signal sequence. Also contained $Amp^R$. | This application |
| pET2 | Cloning intermediate based on pET11d that contain the mmoX promoter linked to the sequence encoding the MopE signal sequence and the $mopE^{H*}$ gene. Also contained $Amp^R$. | This application |
| pBBR1MCS-2 | Used as vector for the $mopE^{H*}$ gene. Contained mob genes, thus were mobilizable when tra genes were provided by E. coli S17-1. Also contained lacZα, $Km^R$ and rep. | Kovach et al., 1995 |
| pBBmopE$^{H*}$ | Used to express $mopE^{H*}$ in E. coli S17-1 and to transfer $mopE^{H*}$ to M. capsulatus ΔmopE. Vector based on pBBR1MCS-2 containing a truncated mopE, $mopE^{H*}$, the mmoX promoter and the sequence encoding the MopE signal sequence. Also contained $Km^R$. | This application |

Primers

TABLE 4

List of primers used.

| Name | Sequence | Use |
|---|---|---|
| sMMOprSacI | 5'-GTGGAGCCGTTGCCGTTC CGGTTCAGCGTGTCC-3' | PCR amplification of mmoX promoter linked to the sequence encoding the MopE signal sequence |
| MopEXhoR | 5'-TGGCGGTGATCTCGAGCC TGC-3' | PCR amplification of mmoX promoter linked to the sequence encoding the MopE signal sequence |
| spNcoI | 5'-AGTGCCTCCATGGGCGGC TG-3' | PCR amplification of the $mopE^{H*}$ gene. |
| MopE*NcoI | 5'-CAGCGAACTCCCATGCC TGGAC-3' | PCR amplification of the $mopE^{H*}$ gene. |

Eurogentec supplied all primers, except from MopEXhoR supplied by TAGN Ltd and M13 forward supplied by Invitrogen.

Kits

TABLE 5

List of kits used.

| Kit | Use | Supplier |
|---|---|---|
| QIAQuick Miniprep | Purification of plasmid DNA | QIAGEN |
| QIAGEN HiSpeed Midi Plasmid Purification Kit | Large scale purification of plasmid | QIAGEN |
| PCR purification Kit | Purification of PCR products | QIAGEN |
| TOPO TA cloning Kit | Subcloning of PCR products | Invitrogen |

TABLE 5-continued

List of kits used.

| Kit | Use | Supplier |
| --- | --- | --- |
| QIAQuick Gel Extraction KIt | Extraction of DNA from agarose gels | QIAGEN |
| ECL western blotting detection system | Development of immunoblot | Amersham Bioscience |

Transfer of Plasmid DNA to *M. capsulatus* by Conjugation

Presently conjugation is the only method available for transfer of genetic information to *Methylococcus*. Conjugative transfer require establishment of physical contact between the cells of the mating-pair, the DNA donor and the DNA recipient. Additionally, the donated plasmids must hold mob or tra genes. The plasmid used, pBBR1MCS-2 (Table 3-3), contained mob genes, while *E. coli* S17-1 contained tra genes.

Conjugation was performed as described by Lloyd et al (1999) using the plasmids derived from the mobilizable plasmid pBBR1MCS-2 and the mating-pair donor *E. coli* S17-1.

*M. capsulatus* and *E. coli* whole cells were then separated from the spent medium by centrifugation.

Concentration of Spent Medium Proteins by Cellulose Ultrafiltration

MopE* is the major protein detectable in unconcentrated spent medium of *M. capsulatus* cultures. Spent medium proteins were concentrated by cellulose ultrafiltration using the Amicon® Ultra-15 PL-100 centrifugation filter device. The filter used had a nominal molecular weight limit of 10 kDa and maximum sample volume of 15 ml. Spent medium from a 150 ml cultures was concentrated to a final volume of about 200 µl by repeated centrifugations.

Strategy for Cloning

Genetic manipulation in *M. capsulatus* imposes several constraints regarding systems available for genetic transfer. Conjugation is the only method known to be effective in transferring genes to *M. capsulatus*, thus the conjugative vector, pBBR1MCS-2, was chosen as carrier of the mutated mopE genes. Based on its successful use in prior conjugations to *M. capsulatus*, *E. coli* S17-1 was chosen as plasmid DNA donor. When this study was initiated expression vectors compatible with *M. capsulatus* were not available. Thus, to enable initiation of transcription in *M. capsulatus*, a promoter recognizable by this bacterium was connected to the mutated mopE genes in the conjugative plasmids. Moreover, it was desirable that the transcription should be regulated in a relatively easy manner and this led to use of the mmoX promoter. The mmoX promoter initiate transcription of the *M. capsulatus* (Bath) operon mmoXYBZYC, and its activity is affected by the concentration of copper. The promoter region used was the 335 bp region located immediately upstream of the start-codon of mmoXYBZYC. This region has been shown to be sufficient for the copper-dependent activity of the promoter.

Construction of the mopE$^H$* Gene that Encodes the MopE$^H$* Mutant Protein

Figure 3:
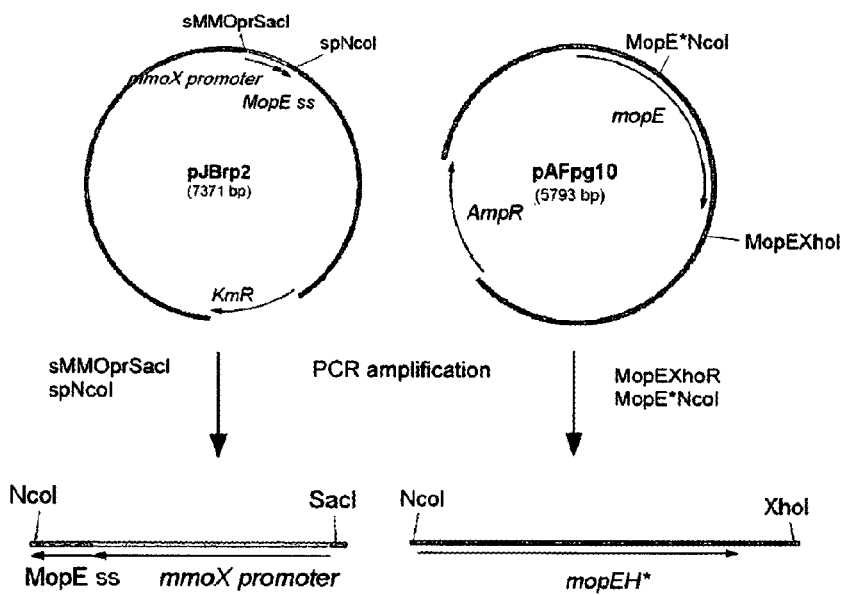
FIG. 3. Amplification of DNA molecules containing the mopE$^{H}$* gene or the mmoX promoter linked to the sequence encoding the MopE signal sequence from pAFpg10 or pJBrp2, respectively. The mopE$^{H}$* gene was constructed by amplification of a region of pAFpg10 using the primers MopEXhoR and MopE*NcoI. The DNA containing the copper sensitive mmoX promoter and the sequence encoding the MopE signal sequence (MopE ss) was amplified from pJBrp2 using the primers sMMOSacI and spNcoI.

The mopE gene was contained in pAFpg10 (Table 3.), and this plasmid was purified from cells from an *E. coli* DH5α culture. The deletion mutant of the mopE gene was constructed by PCR amplification (FIG. 3) using the forward primer MopE*NcoI (Table 4.) and the reverse primer MopEXhoR (Table 4.). The resulting amplified fragment (FIGS. 3 and 4) was ~1.2 kb and consisted of a DNA encoding MopE* ($Gly_{205}$-$Pro_{540}$), as well as a downstream region containing a Rho-independent transcription terminator. By using primers slightly non-complimentary to their target sequences, flanking NcoI and XhoI recognition sites were introduced in this amplified product. The introduction of the 5' NcoI site resulted in addition of an additional histidine codon to the 5'-end of the mopE* gene. Thus, the amplified gene constructed and the protein encoded by it, was designated mopE$^H$* and MopE$^H$*, respectively.

The mmoX promoter was present in the plasmid pJBrp2 (Table 3.) linked to the sequence encoding the MopE signal sequence. This plasmid was purified from *E. coli* DH5a cells (Table 2.), and a fragment containing the mmoX promoter linked to the sequence encoding the MopE signal sequence was amplified from pJBrp2 by the PCR using the primers spNcoI (Table 4.) and sMMOprSacI (Table 4. and FIG. 3). The resulting ~0.5 kb DNA product (FIG. 4) was flanked by SacI and NcoI restriction sites.

Figure 5:
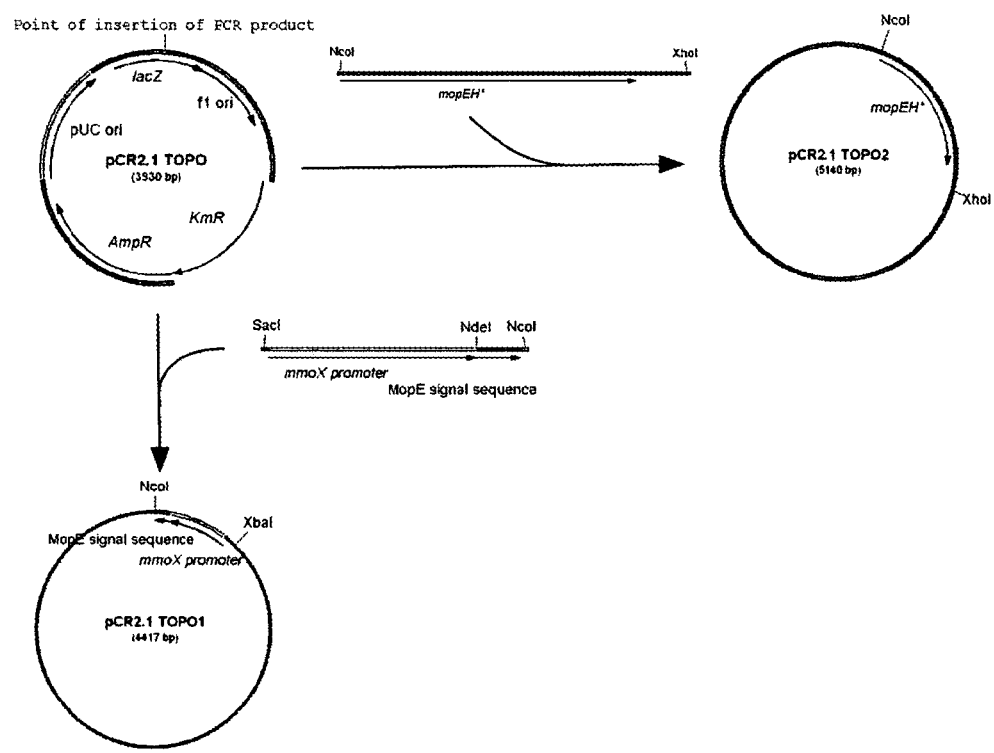
FIG. 5. Subcloning of the amplification products in pCR®2.1-TOPO vectors by TOPO® TA cloning. The DNA containing the mmoX promoter linked to the sequence encoding the MopE signal sequence was inserted to pCR2.1-TOPO to produce pCR2.1-TOPO1, while the DNA containing the mopE$^{H}$* gene was inserted to pCR2.1-TOPO to produce pCR2.1-TOPO2.

To simplify handling of the amplified fragments, the two amplification products were individually cloned into pCR® 2.1-TOPO vectors (Table 3) by TOPO® TA cloning producing pCR2.1-TOPO1 and pCR2.1-TOPO2 (FIG. 5). Transformants from both the TOPO® TA reactions were selected based on their resistance to ampicillin and impaired production of β-galactosidase. A high yield of transformants was obtained from both transformation reactions.

Figure 4:
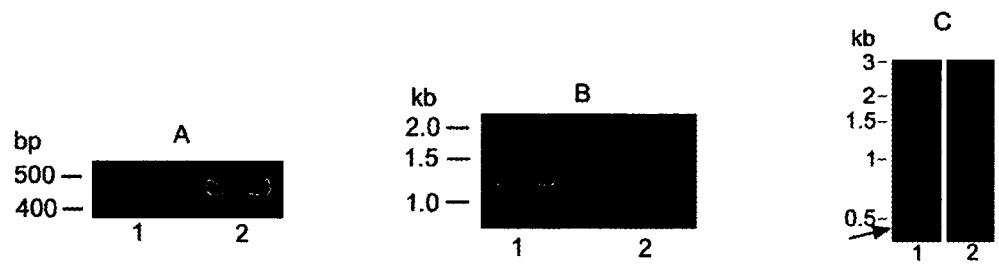
FIG. 4. Amplification DNAs containing the mopE$^{H}$* gene or the mmoX promoter linked to the sequence encoding the MopE signal sequence. Negative PCR controls used had composition identical to the PCR sample except that no template was added. (A) PCR amplification of the ~0.5 kb DNA containing the mmoX promoter linked to the sequence encoding the MopE signal sequence (lane 2) and PCR negative control (lane 1). (B) PCR amplification of a ~1,2 kb DNA containing the mopE$^{H}$* gene (lane 1) and PCR negative control (lane 2). (C) The amplified DNAs were subcloned in pCR2.1-TOPO vectors, and resulting plasmids were controlled by RE-analysis. NcoI/XhoI digested pCR2.1-TOPO1 (lane 1) and pCR2.1-TOPO2 (lane 2).

A few single colonies of transformants were picked and cultivated in liquid LB. Cells from the *E. coli* TO10F' cultures were harvested, plasmids were purified and analyzed by NcoI and SacI digestion (FIG. 4 C). All plasmids purified from the TOPO® TA cloning reaction with the ~0.5 kb PCR product were digested into three fragments of lengths ~0.5 kb, ~1.5 kb and ~2.5 kb, while all the plasmids purified from the TOPO® TA cloning reaction with the ~1.2 kb PCR product were digested into three fragments of lengths ~1.2 kb, ~1.5 kb and ~2.5 kb (FIG. 4 C lane 1-2, respectively). Thus, the results of the RE-analyses were in agreement with theoretical predictions. One *E. coli* TO10F' colony containing pCR2.1-TOPO1 and one colony containing pCR2.1-TOPO2 were selected for further analysis. Plasmids from these colonies were purified and sequenced. This sequencing confirmed that the fragment containing the mmoX promoter linked to the MopE signal sequence fragment was contained in pCR® 2.1-TOPO1, and that the fragment containing the mopE$^H$* gene was contained in pCR® 2.1-TOPO2.

Figure 2:
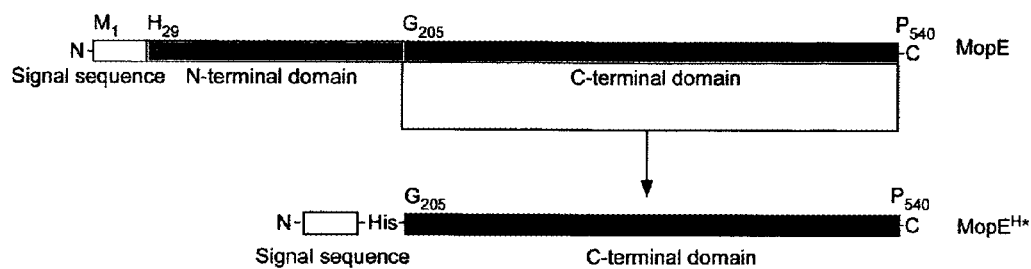
FIG. 2. Overview of the structure of MopE and MopE$^{H*}$. MopE consists of two domains, the non-secreted N-terminal domain and the secreted C-terminal domain, in addition to a Sec-dependent signal sequence. In MopE$^{H*}$ the histidine originating from the cloning strategy is shown.
Figure 6:
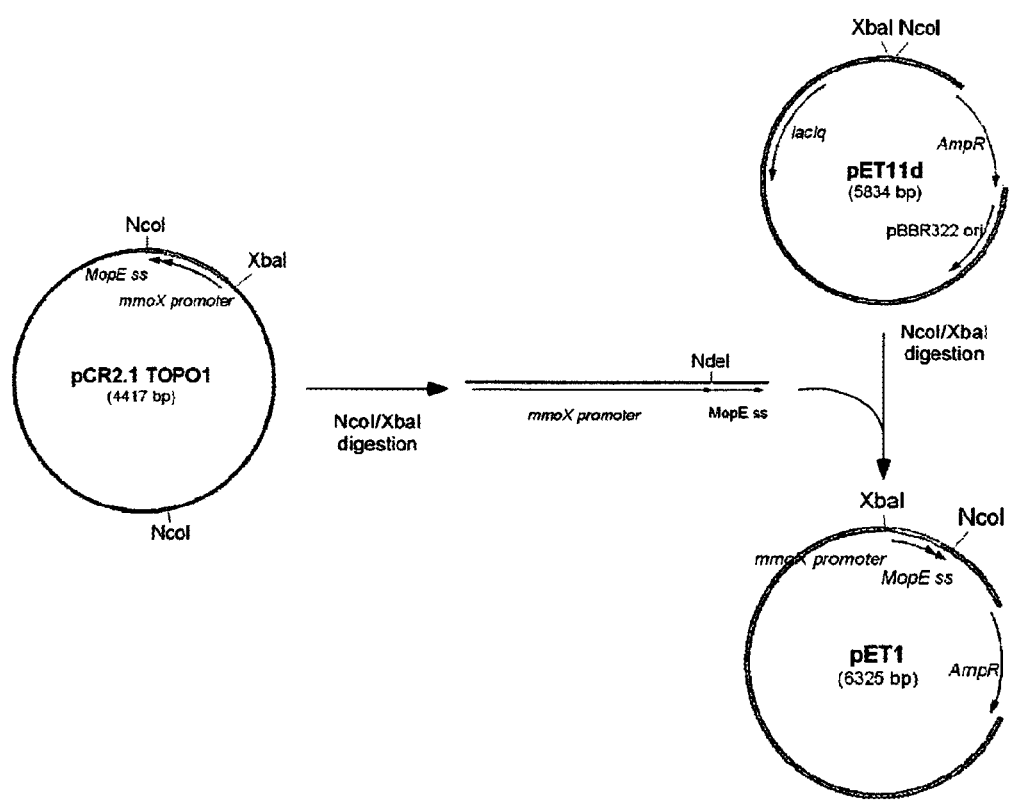
FIG. 6. Subcloning of the DNA containing the mmoX promoter linked to the sequence encoding the MopE signal sequence in pET11d. The DNA containing the mmoX promoter and the sequence encoding the MopE signal sequence was inserted to pET11d, producing pET1.

Because of incompatibility of RE-sites in plasmid and fragments, the mopE$^H$* gene could not be connected to the mmoX promoter and the sequence encoding the MopE signal sequence directly in the conjugative vector pBBR1MCS-2. Thus, the fragments should be subcloned in pET11d (Table 4.). First, the DNA containing the mmoX promoter linked to the sequence encoding the MopE signal sequence should be inserted to pET11d (FIG. 6) to produce pET1 (Table 3). The DNA containing the mopE$^H$* gene then should be inserted to pET1 to produce pET2 (Table 3). Thus, in pET2 the mmoX promoter should precede the mopE$^{H}$* gene connected with an upstream sequence encoding the MopE signal sequence (FIG. 2).

Figure 7:
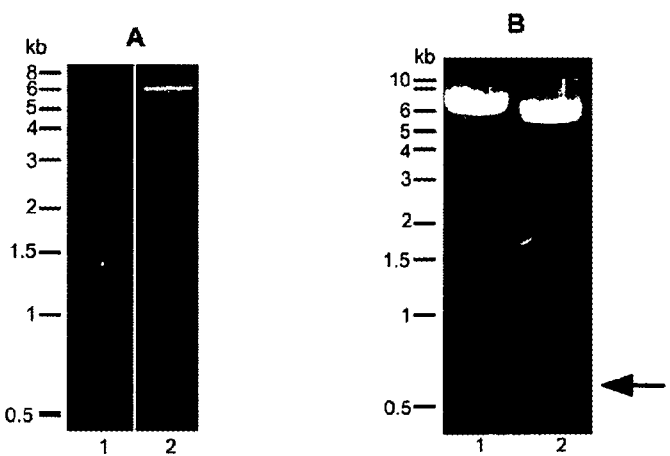
FIG. 7. Construction of and RE-analysis of pET1 (A) The ~0.5 kb DNA containing the mmoX promoter linked to the sequence encoding the MopE signal sequence (lane 1) and the ~5.9 kb pET11d vector fragment (lane 2) were purified from an agarose gel. (B) pET1 was digested by BamHI (lane 1) and double digested with NcoI and XbaI (lane 2).

As a first step to construct pET1, both pCR® 2.1-TOPO1 and pET11d were digested by NcoI and XbaI. The restriction of pCR2.1-TOPO1 produced three fragments with lengths ~0.5 kb, ~1.7 kb and 2.3 kb, while restriction of pET11d produced a ~5.8 kb fragment, all in agreement with the theoretical predictions. The ~0.5 kb DNA containing the mmoX promoter linked to the sequence encoding the MopE signal sequence and the ~5.9 kb vector fragment were purified from the preparative agarose gel (FIG. 7 A lane 1-2), and used in a subsequent ligation reaction. The ligation solution was used to transform E. coli TOP10F' cells and the resulting transformants were selected based on their resistance to ampicillin. One colony of transformed E. coli TOP10F' cells was obtained. The transformed colony was cultivated in a 5 ml LB culture. A plasmid, designated pET1, was purified from the cells and analysed by RE digestion. The length of pET1 was estimated to be about 6.3 kb by agarose gel electrophoresis (FIG. 7 B lane 1). In agreement with theoretical predictions pET1 to produced two bands, one of length ~5.8 kb and one of ~0.5 kb after NcoI/XbaI double digestion (FIG. 7 B lane 2). Insertion of the mmoX promoter and the sequence encoding the MopE signal sequence were verified by sequencing.

Figure 8:
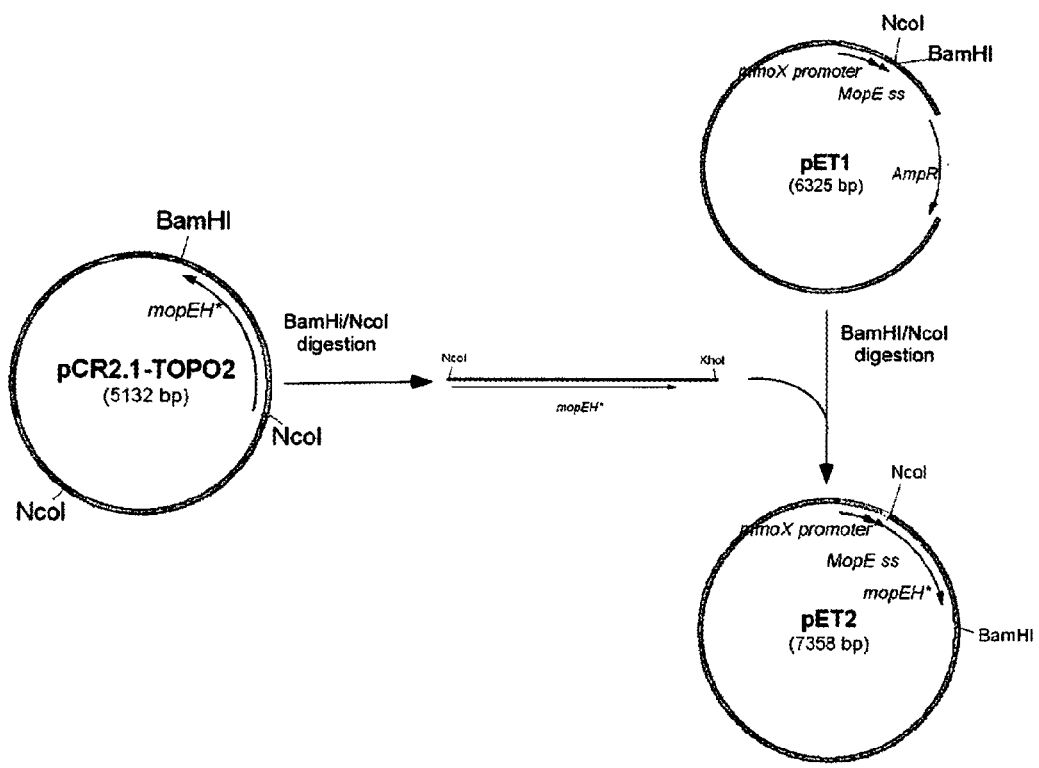
FIG. 8. Subcloning of the DNA containing the mopE$^{H}$* gene in pET1. To produce pET2 a DNA containing the mopE$^{H}$* gene was inserted to pET1.

To produce pET2 the DNA containing the mopE$^{H}$* gene was inserted to pET1 (FIG. 8). The DNA containing the mopE$^{H}$* gene was excised from pCR® 2.1-TOPO2 by digestion with BamHI and NcoI and this resulted in three fragments with apparent lengths of ~1.2 kb, ~1.6 kb and ~2.3 kb, as theoretically predicted. The plasmid pET1 was opened by digestion with BamHI and NcoI and this resulted in a linear vector fragment of about 6.3 kb.

Figure 9:
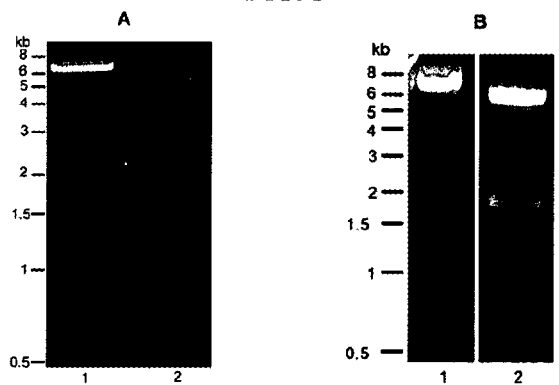
FIG. 9. Construction of and RE-analysis of pET2. (A) A ~1.2 kb DNA containing the mopE$^{H}$* gene (lane 2) and a ~6.3 kb pET1 fragment (lane 1) were purified from an agarose gel. (B) The pET2 plasmid was digested by BamHI (lane 1) and double digested by BamHI and NcoI (lane 2).

The ~1.2 kb DNA containing the mopE$^{H}$* gene and the ~6.3 kb pET1 fragment were purified from a preparative agarose gel (FIG. 9 A lane 1 and 2, respectively) and used in a subsequent ligation reaction. The ligation solution was used to transform E. coli TOP10F' cells and transformants were selected based on resistance to ampicillin. A generous number of colonies of transformed E. coli TOP10F' cells were obtained. A few colonies were picked and cultivated in liquid media for further analysis. Plasmids, designated pET2, were purified from the selected transformed cells and analysed by RE digestion. As predicted theoretically the length of the pET2 was estimated to be ~7.4 kb by agarose gel electrophoresis (FIG. 9 B lane 1). Double digestion of the plasmid with BamHI and XbaI produced two DNAs, one ~1.7 kb and one ~5.7 kb fragment (FIG. 9 B lane 2), as theoretically predicted. Sequencing confirmed that the mopE$^{H}$* gene, in pET2, was preceded by the mmoX promoter and the sequence encoding the MopE signal sequence.

Figure 10:
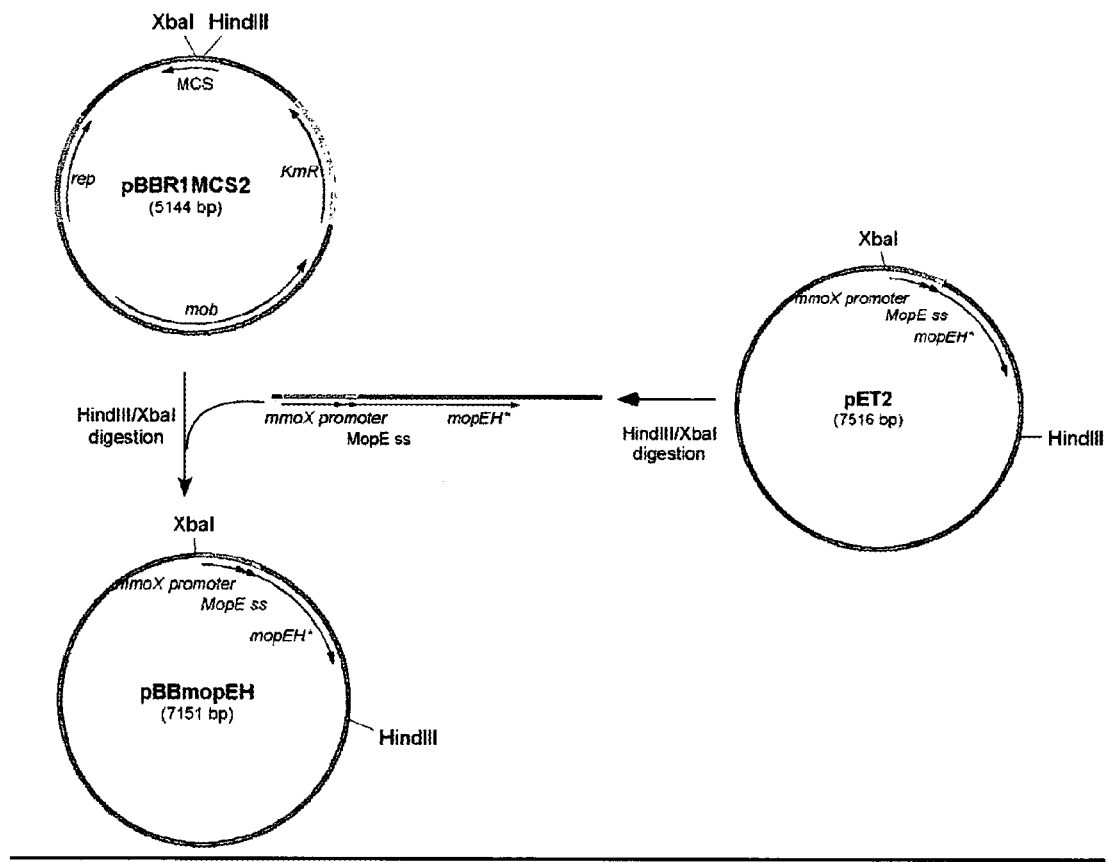
FIG. 10. Construction of pBBmopE$^{H}$*. A pET2-DNA containing the mopE$^{H}$* gene, the mmoX promoter and the sequence encoding the MopE signal sequence was excised from pET2 an inserted to pBBR1MCS-2 to produce pBBmopE$^{H}$*.

From pET2 a DNA fragment containing the mopE$^{H}$* gene proceeded by the sequence encoding the MopE signal sequence and the mmoX promoter could be excised and transferred to the mobilizable vector pBBR1MCS-2 (Table 3.). This would produce pBBmopE$^{H}$*(FIG. 10). The pBBmopE$^{H}$* amino acid sequence is shown in the sequence listing, as SEQ. ID. NO 9.

This pET2-DNA fragment was excised from the plasmid by restriction with HindIII and XbaI. As theoretically predicted this resulted in two DNAs, one of ~2.0 kb and one of ~5.5 kb. Also as expected, opening of pBBR1MCS-2 by digestion with HindIII and XbaI produced a ~5.1 kb vector-DNA. The ~5.1 kb vector-DNA was purified from a preparative agarose gel along with the ~2.0 kb pET2-DNA containing the mmoX promoter linked to the sequence encoding the MopE signal sequence and the mopE$^{H}$* gene (FIG. 11 A lane 1 and 2) and were ligated. The ligation solution was subsequently used to transform E. coli Top10F' cells, and transformed cells were selected based on their resistance to kanamycin. A total of 26 colonies of transformed E. coli Top10F' cells were obtained. A few colonies of transformants were cultivated in 5 ml cultures for further analysis.

Figure 11:
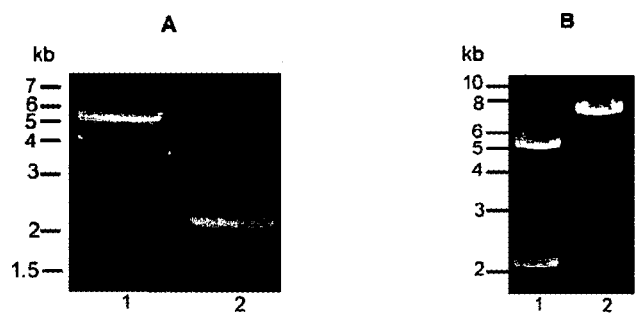
FIG. 11. Construction and RE-analysis of pBBmopE$^{H}$*. (A) The ~5.1 kb pBBR1MCS-2 fragment (lane 1) and ~2.0 kb pET2 (lane 2) were purified from a preparative agarose gel. (B) The pBBmopE$^{H}$*plasmid was double digested with BamHI and XbaI (lane 1) and single digested by NdeI (lane 2).

Plasmids, designated pBBmopE$^{H}$*, were purified from the selected transformed cells and analysed by RE digestion. As theoretically predicted the length of pBBmopE$^{H}$* was estimated to be about 7.2 kb by agarose gel electrophoresis (FIG. 11 B lane 2), while double digestion of pBBmopE$^{H}$* with BamHI and XbaI produced two DNAs, a ~2.0 kb and a ~5.1 kb DNA (FIG. 11 B lane 1). That pBBmopE$^{H}$* contained a mopE$^{H}$* gene preceded by the mmoX promoter and the sequence encoding the MopE signal sequence was confirmed by sequencing.

Production of MopE$^{H}$* in E. coli S17-1

A previous study in our laboratory has shown that the mmoX promoter is functional in E. coli. The expression of the mutated mopE$^{H}$*gene was studied in E. coli prior to transfer of the gene to M. capsulatus. E. coli whole cells and spent media were analysed by immunoblotting. E. coli S17-1 cells harbouring pBBmopE$^{H}$* were harvested from 50 ml cultures and By immunoblotting one immunoreactive protein migrating according to an apparent molecular mass of about 50 kDa was detected (not shown), thus the protein migrated shorter than wild type MopE* in the gel. Thus the E. coli host cell apparently produced MopE$^{H}$*, but the host was not able to cleave off the signal peptide. As expected no immunoreactive proteins were detected in the E. coli S17-1 cells harbouring pBBR1MCS-2 (not shown).

Spent medium from a culture of E. coli S17-1 harbouring pBBmopE$^{H}$* was concentrated. No immunoreactive proteins were detected in the concentrated spent medium. Thus, MopE$^{H}$* were seemingly not secreted from E. coli S17-1 in detectable amounts. As expected, the E. coli S17-1 pBB1MCS-2 did not either secrete immunoreactive proteins.

Production of MopE$^{H}$* in M. capsulatus ΔmopE

The pBBmopE$^{H}$* plasmid was transferred to M. capsulatus:

The plasmid was transferred from E. coli S17-1 to M. capsulatus ΔmopE by conjugation and M. capsulatus cells transformed by pBBmopE$^{H}$* were selected by their resistance to kanamycin and gentamycin. A total of four conjugants were obtained. A few were selected for further analysis. The pBBmopE$^{H}$* plasmid was purified from the selected transformants and re-sequencing confirmed that no deletions had occurred during the conjugation process.

To study the expression of MopE$^{H}$* in M. capsulatus the copper-sensitive mmoX promoter was induced by cultivation of M. capsulatus ΔmopE containing pBBmopE$^{H}$* in a copper-depleted medium. Cells were separated from the spent medium by centrifugation, No MopE proteins could be detected in the M. capsulatus ΔmopE cells harbouring the empty conjugative plasmid, and no MopE protein was secreted from these cells.

Figure 12:
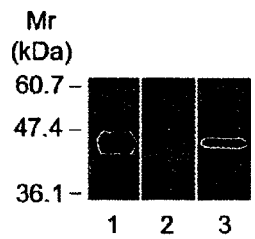
FIG. 12. ECL developed blot of spent media of a copper-depleted *M. capsulatus* (Bath) wild type culture (lane 1) and of copper-depleted cultures of *M. capsulatus* ΔmopE harbouring either pBBR1MCS-2 (lane 2) or pBBmopE$^{H}$* (lane 3).

The spent medium was isolated from the M. capsulatus ΔmopE pBBmopE$^{H}$* cell, concentrated and subjected to SDS-PAGE and immunoblotted. One immunoreactive protein was detected (FIG. 12 lane 3). This protein migrated as wild type MopE* (FIG. 12 lane 1), demonstrating that MopE$^{H}$* was secreted from M. capsulatus ΔmopE. Thus, the protein was properly processed in M. capsulatus and was able to cross the OM even though the N-terminal domain had been removed.

In conclusion, MopE$^{H}$* was expressed both in E. coli 517-1 and in M. capsulatus ΔmopE, but the secretion of MopE$^H$* was host specific, as MopE$^H$* was detected in the spent medium of the *M. capsulatus* culture only. This shows conclusively the ability of MopE$^H$* to translocate across the outer membrane of *M. capsulatus*.

The inventors have in a previous application (Norwegian Patent Application No. 20033176) established a fusion protein of the complete MopE from *M. capsulatus* and the VP2 protein in of the infectious pancreatic necrosis (IPN) virus. They have also demonstrated that it is possible to express heterologous peptides in *M. capsulatus* by using the native protein MopE as a fusion partner. These fusion proteins did translocate, and produced immunological active antibodies.

Figure 13:
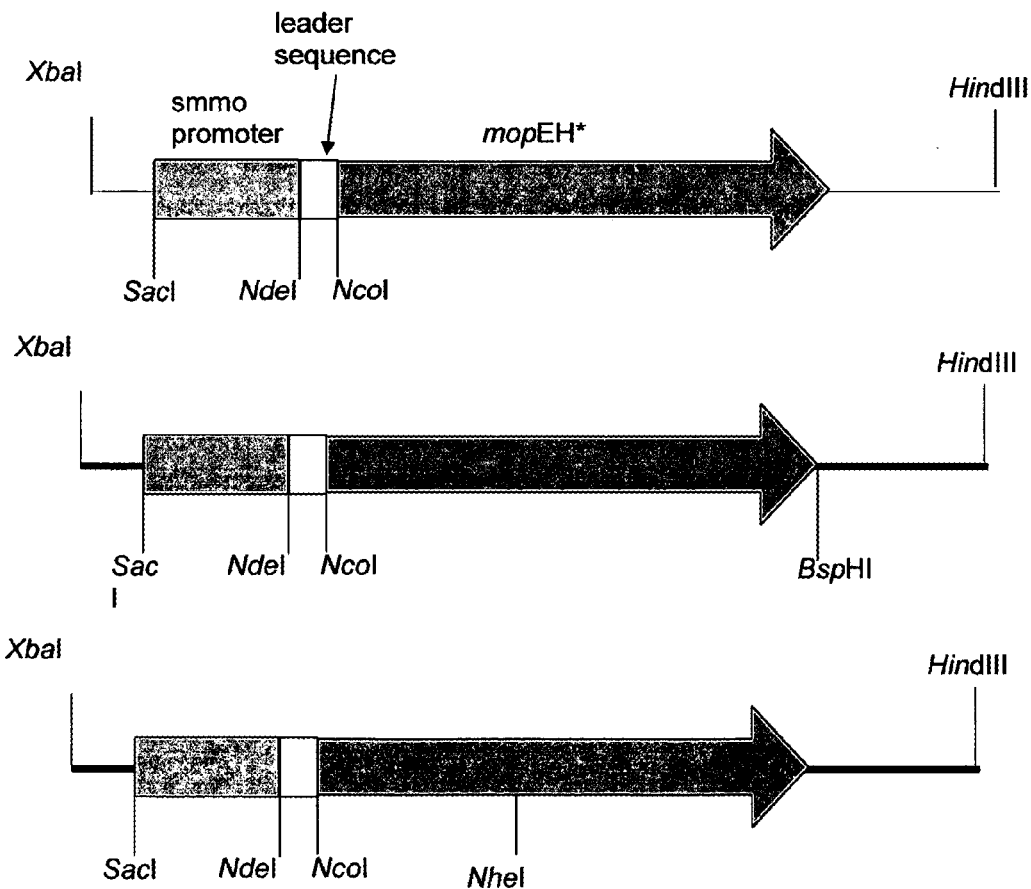
FIG. 13. Diagrams of MopEH*, and MopEH* modified to contain restriction sites for BspHI and NheI, in order to facilitate cloning of fusion proteins.
Figure 14:
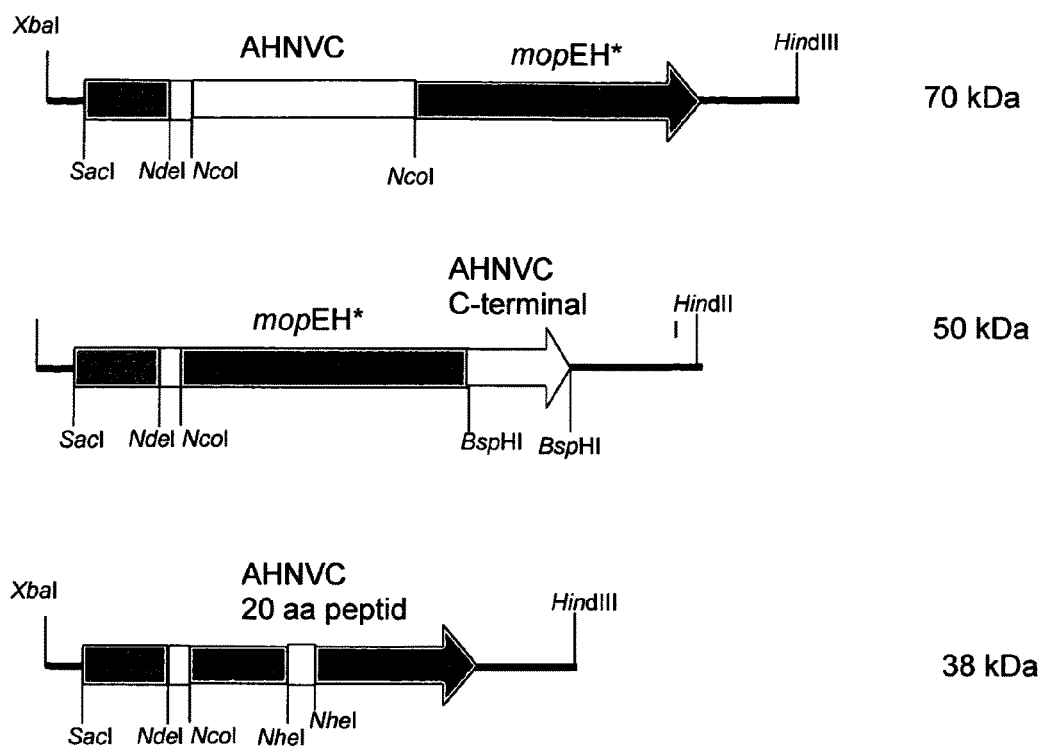
FIG. 14. The three MopEH*-nodavirus constructs developed: AHNVC-MopEH*, MopEH*-AHNVCc and MopEH*-AHNVC-20.

MopEH* sequence contains a BspHI site at the stop codon of MopEH*, another one a NdeI site internally in MopEH*, causing some minor changes in the MopEH* sequence. The DNA sequences of these two specific modified MopEH* sequences are fiven as SEQ. ID. NO. 16 and 17, respectively. Diagrams thereof are shown in FIG. 13. Three MopEH*-nodavirus capsid constructs were made, as shown in FIG. 14.

DNA from Atlantic halibut Nodavirus was a gift from Audun Nerland. Based on the published capsid sequence (Accession number AJ245641, SEQ. ID. NO. 18_in the attached patentIn file) the primers listed in Table 6 were ordered from Sigma-Aldrich.

TABLE 6

List of primers used to create the Atlantic halibut Nodavirus capsid and MopEH* fusion proteins

| Primer | Sequence | Comment |
|---|---|---|
| AHNVC-F_NcoI | GCAAACCATGGTAAGAAATTGGCTAAACCAGCGACCAC | Contains a NcoI restriction enzyme site |
| AHNVC-R_NcoI | TTAGTCCATGGAGTCAGCTCGGGTGTTGAG | Contains a NcoI restriction enzyme site |
| AHNVC-mopE-mut1 | GCCATGGgAGTCAGCTCGGGTGTTGAG | Inserts a C-residue to correct a phase shift in the mopEH* sequence |
| AHNVCC-F_BspHI | TCATGATACATTCGCTCCAATCCTAAC | Contains a BspHI restriction enzyme site |
| AHNVC-R_BspHI | TTAGTCTCATGAGTCAGCTCGGGTGTTGAG | Contains a BspHI restriction enzyme site |
| AHNVCC_BspHI a mut | CTCCAAGCCTACATTCGCTCC | Corrects a frame shift in the mopEH*-AHNVCC fusion sequence |
| AHNV 20 aa peptide fwd | CTAGCTCATTAGATCGGCCGCTGTCCATTGACTACAGTCTGGGCACTGGTGATGTCGACCGTGCCG | Forward strand of a syntetic 20 amino acid fragment of AHNVC |
| AHNV 20 aa petide rev | CTAGCGGCACGGTCGACATCACCAGTGCCCAGACTGTAGTCAATGGACAGCGGCCGATCTAATGAG | Reverse strand of a syntetic 20 amino acid fragment of AHNVC |
| AHNVCC NheI t mut1 | GCGTGGCTAGCACATTCGCTCC | Corrects a frame shift in the mopEH*-AHNVCC fusion sequence |
| AHNVCC NheI t mut2 | CCGAGCTGACGCTAGCGAGCTC | Corrects a frame shift in the mopEH*-AHNVCC fusion sequence |

Cloning of Nodavirus Capsid—MopEH* Fusion Proteins

In order to ascertain whether MopE$^H$* is able not only to translocate itself, but to do so as a functional fusion protein, several constructs with Nodavirus capsid protein were constructed, and the expression thereof was tested.

Atlantic halibut nodavirus is a RNA virus infecting mitochondria of insects or fish. It infect halibut at the larvae or juvenile stage, and mortality rates are up to 100%. Antibodies against AHNV have been previously developed.

The cloning of the fusion protein constructs were achieved by conventional methods, including standard lab methods and commercial kits for cloning, mutagenese, immunoblotting etc, using pBBR1MCS2, as described above, as the starting plasmid. This time, instead of cloning in the MopE$^H$* nucleotide sequence alone, the sequence was first modified to comprise capsid protein from Atlantic halibut Nodavirus. In order for the capsid protein DNA sequence to be inserted into the MopEH* sequence, the MopEH* sequence was modified to comprise restriction enzyme sites. One such modified Also two new versions of the mopEH* expressions system where made. One version with a BspHI restriction site replacing the stop codon of mopEH* (SEQ ID. NO. 16) and a second version where a NheI restriction site where mutated into a predicted surface loop of MopEH* (SEQ ID. NO. 17). The mopEH* plasmids are base don the pBBR1-MCS2 plasmid, and SEQ ID. NO. 19 shows the original, unmodified pBBR1-mopEH*.

In the first construct, AHNVC-MopEH*, the known sequence of Atlantic halibut Nodavirus capsid protein (AHNVC) were fused to MopEH* using the NcoI restriction enzyme site at the start of MopEH* giving a protein of 72.4 kDa. The leader sequence should be cleaved off when exported from the cytoplasm giving a protein of 72.5 kDa. The DNA and protein sequences of AHNVC-MopEH* are given as SEQ. ID. NO. 10 and 11, respectively.

In the second construct, MopEH*-AHNVCc, the predicted surface part of Atlantic halibut Nodavirus capsid protein (AHNVCc) were fused to MopEH* using the BspHI restriction enzyme site at the end of MopEH* giving a protein of 52.5 kDa. The leader sequence should be cleaved off when exported from the cytoplasm giving a protein of 49.5 kDa. The DNA and protein sequences of MopE*-AHNVCc are given as SEQ ID. NO. 12 and 13, respectively.

In the third construct, MopEH*-AHNVC-20, aa a 20 amino acid fragment of Atlantic halibut Nodavirus capsid protein (AHNVC-20aa) were inserted into a predicted surface loop of MopEH* using the NdeI restriction enzyme site giving a protein of 41.5 kDa. The leader sequence should be cleaved off when exported from the cytoplasm giving a protein of 38.5 kDa. The DNA and protein sequences of MopEH*-AHNVC-20aa are given as Seq. ID no 14 and 15, respectively.

Expression of Atlantic Halibut Nodavirus Capsid MopEH* Recombinant Proteins

The tree recombinant proteins where conjugated into *M. capsulatus* ΔmopEH*. To express the recombinant protein *M. capsulatus* ΔmopEH were grown in a low copper medium. At late log phase growth the cultures were harvest and fractionated into:

1: Spent medium (S)
2: Periplasmic fraction (P)
3: Cytoplasmic fraction (C)
4: Inner membrane (I)
5: Outer membrane (O)

Figure 15:
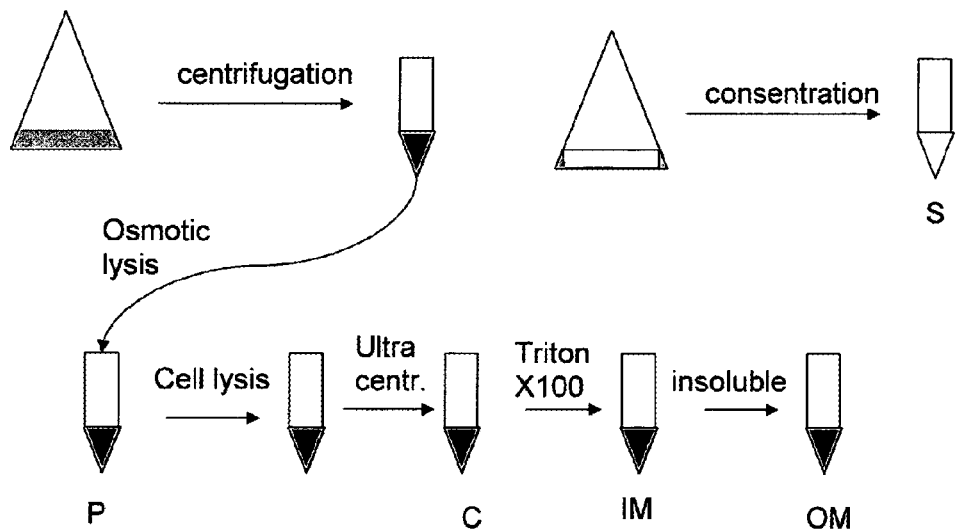
FIG. 15. Schematic of the determination of the localization of recombinant MopEH*

FIG. 15 shows the scheme for localization of the recombinant MopEH*.

Figure 16A:
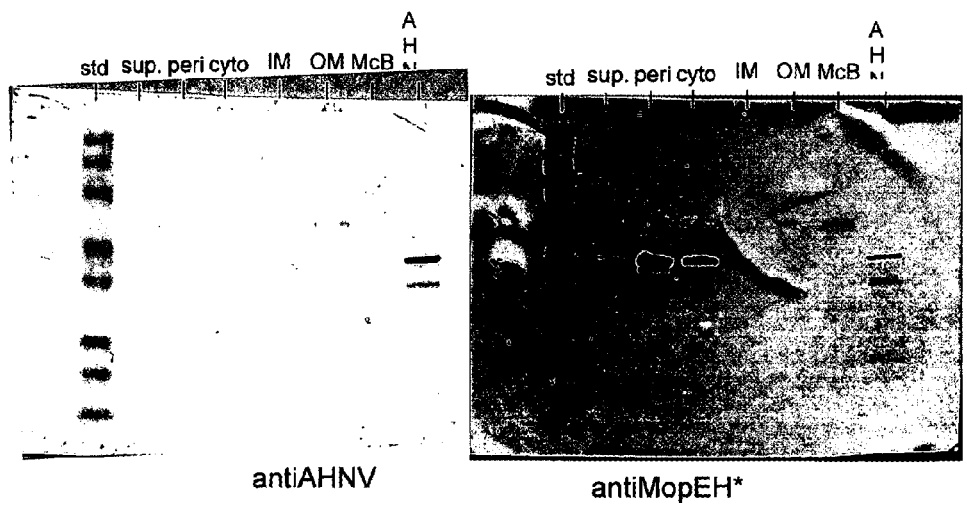
FIG. 16. Gel results of MopEH*-AHNVCc (16a) and MopEH*-AHNVC-20 (16b) and AHNVC-MopEH* (16c) using anti-AHNVC and anti-MopEH*.
Figure 16B:
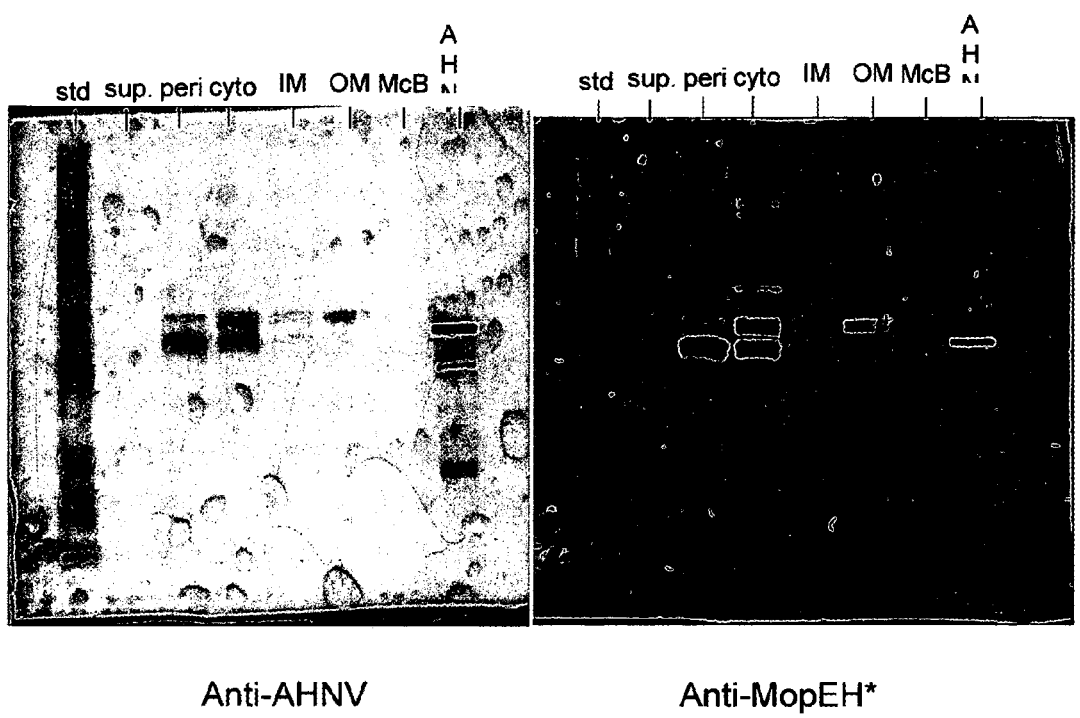
Figure 16C:
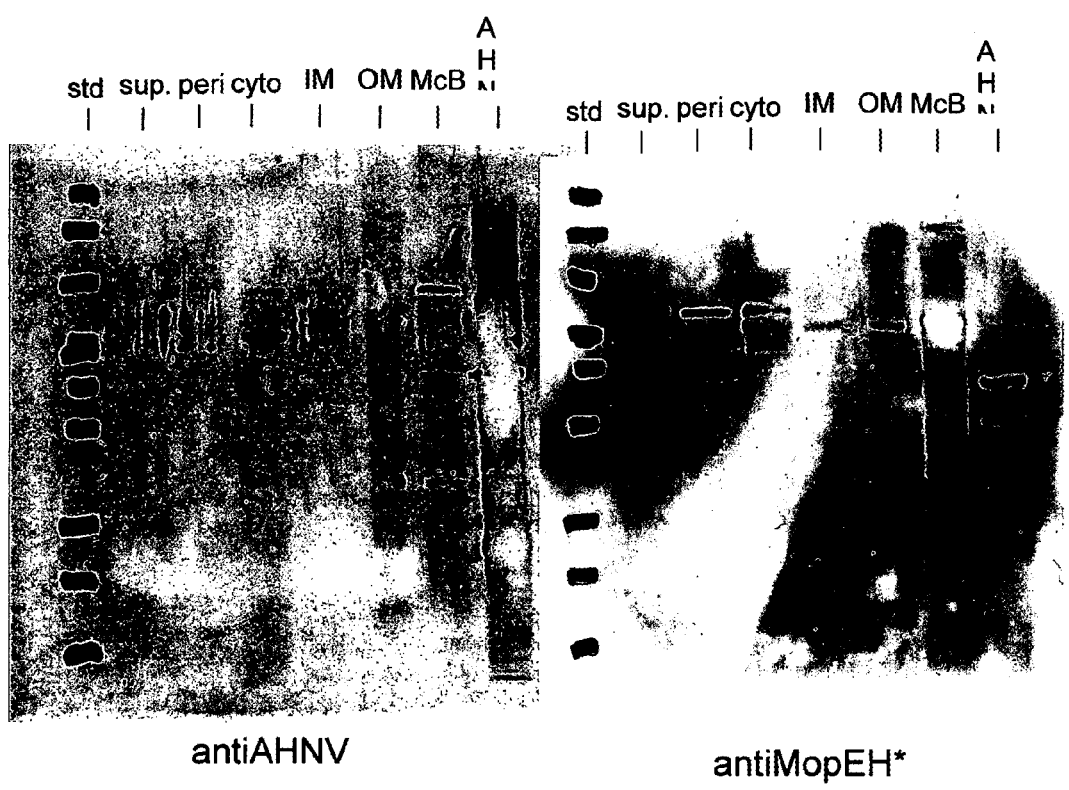

The presence of recombinant protein where checked with protein-immunoblot using either AHNV antibodies or MopEH antibodies. The results are given in FIG. 16. As can bee seen in FIG. 16 a, for the MopEH*-AHNVCc construct the majority of recombinant MopEH*-AHNVcc was degraded to MopEH*, although some intact fusion protein is left FIG. 16*b* shows that for the MopEH*-AHNVC 20 aa peptide the MopEH*-AHNVC seems to be misfolded. FIG. 16*c* shows that the AHNVC-MopEH* seems to be intact, although the plasmid is a bit unstable.

Figure 17:
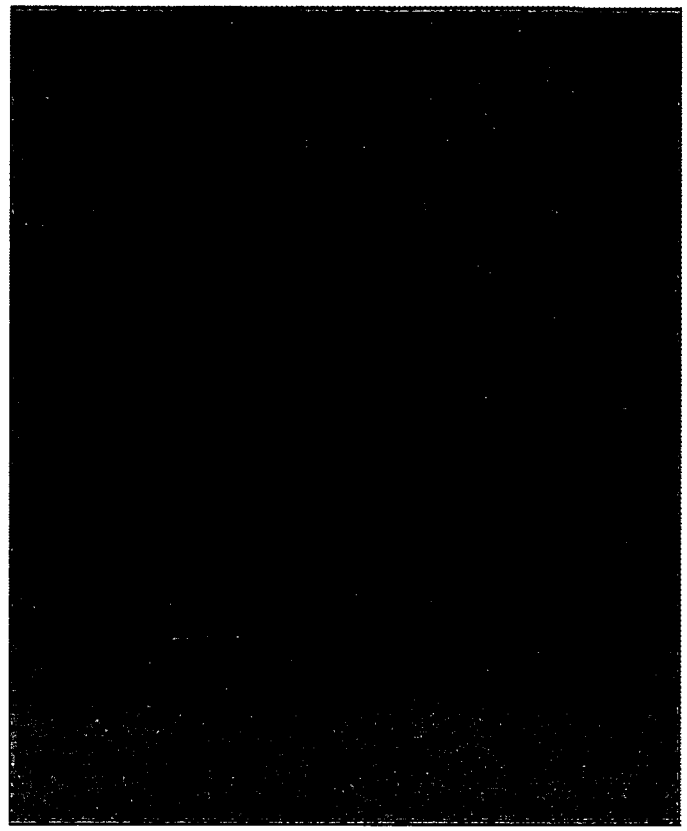
FIG. 17. Use of antibodies against MopEH*-AHNVC 20 aa peptide shows that the construct is antigenic.

FIG. 17 shows the results of using antibodies against the MopEH*-AHNVC 20 aa peptide. This clearly shows that the translocated MopEH*-AHNVC is antigenic.

In conclusion, the above results thus show that MopEH* fusion proteins can be successfully constructed, and successfully translocated thrugh the outer membrane of *M. capsulatus* and there expressed.

The invention claimed is:

1. A recombinant expression vector comprising a promoter, a coding sequence having multiple cloning sites operably linked to and under the control of the promoter, an intron having the nucleotide sequence set forth as SEQ ID NO. 4 or a nucleotide sequence at least 95% identical to SEQ ID NO. 4 fused with a nucleotide sequence coding for a desired protein or peptide, said intron being operably linked to the coding sequence.

2. The recombinant expression vector according to claim 1, wherein said protein or peptide is a drug, an antigen or an antibody.

3. The recombinant expression vector according to claim 1, wherein said intron further comprises a gene encoding a selection marker.

4. The recombinant expression vector according to claim 3, wherein said selection marker is an antibiotic selection marker.

5. The recombinant expression vector according to claim 1, wherein said expression vector further comprises a replication origin that functions in the host *M. capsulatus*.

6. The recombinant expression vector according to claim 5, wherein said replication origin is smmo or pmmo.

7. The recombinant expression vector according to claim 1, wherein the desired protein is expressed in the host *M. capsulatus*.

8. The recombinant expression vector according to claim 7, wherein the desired protein is expressed on the surface of the outer membrane of *M. capsulatus*.

9. The recombinant expression vector according to claim 8, wherein the nucleotide sequence coding for the desired protein contains a region which codes for a peptide stretch functioning as a substrate for a hydrolyzing enzyme capable of cleaving the desired protein from the remaining outer membrane anchored protein, such that the desired protein is excreted to the culture medium.

10. The recombinant expression vector according to claim 1, wherein the recombinant vector is a plasmid.

11. The recombinant expression vector according to claim 10, wherein the plasmid is SEQ ID NO. 9 or a sequence least 95% identical to SEQ ID NO. 9.

12. The recombinant expression vector according to claim 1, wherein the intron has a nucleotide sequence chosen from the group consisting of Seq ID NO. 10, SEQ ID NO 12, and SEQ ID No 14, fused with a nucleotide sequence coding for a desired protein or peptide.

13. A bacterial host cell transformed with the recombinant vector according to claim 1.

14. The bacterial host cell according to claim 13, wherein the bacterial cell is *M. capsulatus*.

15. A method for producing a desired protein in a bacterial host cell, said method comprising transforming a bacterial host cell with a recombinant expression vector comprising a promoter, a coding sequence having multiple cloning sites operably linked to and under the control of the promoter, an intron having the nucleotide sequence set forth as SEQ ID NO. 4 or a nucleotide sequence at least 95% identical to SEQ ID NO. 4 fused with a nucleotide sequence coding for a desired protein or peptide, said intron being operably linked to the coding sequence and culturing said transformed host cell in a suitable medium under conditions allowing expression of said protein.

16. The method according to claim 15, wherein the method further comprises the step of recovering the expressed protein or peptide from the medium.

17. The method according to claim 15, wherein the host cell is *M. capsulatus*.

18. The method according to claim 15, wherein the desired expressed protein is a drug, wherein said drug is extracted from the host cell, or used together with the host cell for the manufacturing of a vaccine, wherein said vaccine optionally is for oral administration.

* * * * *

UNITED STATES PATENT AND TRADEMARK OFFICE
CERTIFICATE OF CORRECTION

PATENT NO.      : 8,435,760 B2  
APPLICATION NO. : 12/677888  
DATED           : May 7, 2013  
INVENTOR(S)     : Johan R. Lillehaug, Harald B. Jensen and Anne Fjellbirkeland Page 1 of 1

It is certified that error appears in the above-identified patent and that said Letters Patent is hereby corrected as shown below:

On the Title page, item [75]

The correct listing of inventors is thus:

Johan R. Lillehaug, Bergen (NO);
Harald B. Jensen, Eidsvag (NO);
Anne Fjellbirkeland, Blomsterdalen (NO)

Signed and Sealed this
Twenty-eighth Day of July, 2015

Michelle K. Lee
*Director of the United States Patent and Trademark Office*